US009193959B2

(12) United States Patent
Sobek et al.

(10) Patent No.: US 9,193,959 B2
(45) Date of Patent: Nov. 24, 2015

(54) T7 RNA POLYMERASE VARIANTS WITH ENHANCED THERMOSTABILITY

(75) Inventors: Harald Sobek, Penzberg (DE); Johann-Peter Thalhofer, Weilheim (DE); Rainer Mueller, Penzberg (DE); Manfred Schmidt, Penzberg (DE); Michael Greif, Penzberg (DE); Armin Ruf, Freiburg (DE); Christian Rudolph, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 261 days.

(21) Appl. No.: 13/069,514

(22) Filed: Mar. 23, 2011

(65) Prior Publication Data

US 2011/0256589 A1 Oct. 20, 2011

(30) Foreign Application Priority Data

Apr. 16, 2010 (EP) .................................. 10004059

(51) Int. Cl.
*C12N 9/12* (2006.01)
*C12P 19/34* (2006.01)
(52) U.S. Cl.
CPC .................................. *C12N 9/1247* (2013.01)
(58) Field of Classification Search
None
See application file for complete search history.

(56) References Cited

U.S. PATENT DOCUMENTS

| 4,952,496 A | 8/1990 | Studier et al. |
| 6,524,828 B1 | 2/2003 | Liao et al. |
| 7,507,567 B2 * | 3/2009 | Sugiyama et al. ............. 435/194 |

FOREIGN PATENT DOCUMENTS

| EP | 1261696 B1 | 12/2002 |
| WO | 00/36112 A1 | 6/2000 |
| WO | 01/66705 A1 | 9/2001 |
| WO | 2009/113718 A1 | 9/2009 |

OTHER PUBLICATIONS

European Search Report issued Aug. 31, 2010 in European Application No. 10004059.1.
Bonner, Gary et al., "Characterization of a Set of T7 RNA Polymerase Active Site Mutants," The Journal of Biological Chemistry, Oct. 7, 1994, pp. 25120-25128, vol. 269, vol. 40.
Bujard, Hermann et al., "A T5 Promoter-Based Transcription-Translation System for the Analysis of Proteins in Vitro and in Vivo," Methods in Enzymology, 1987, pp. 416-433, vol. 155.
Cheetham, Graham M. T. et al., "Structural basis for initiation of transcription from an RNA polymerase-promoter complex," Nature, May 6, 1999, pp. 80-83, vol. 399.
Cheetham, Graham M. T. and Steitz, Thomas A., "Structure of a Transcribing T7 RNA Polymerase Initiation Complex," Science, Dec. 17, 1999, pp. 2305-2309, vol. 286.
Durniak, Kimmberly J. et al., "The Structure of a Transcribing T7 RNA Polymerase in Transition from Initiation to Elongation," Science, Oct. 24, 2008, pp. 553-557, vol. 322.
Fersht, Alan R. and Serrano, Luis, "Principles of protein stability derived from protein engineering experiments," Current Opinion in Structural Biology, 1993, pp. 75-83, vol. 3.
Griko, Yuri et al., "The Thermal and urea-induced unfolding in T7 RNA polymerase: Calorimetry, circular dichroism and fluorescence study," Protein Science, 2001, pp. 845-853, vol. 10.
Guillerez, Jean et al., "A mutation in T7 RNA polymerase that facilitates promoter clearance," Proceedings of the National Academy of Sciences, Apr. 26, 2005, pp. 5958-5963, vol. 102, No. 17.
He, Biao et al., "Rapid Mutagenesis and Purification of Phage RNA Polymerases," Protein Expression and Purification, 1997, pp. 142-151, vol. 9.
He, Biao et al., "A Mutant T7 RNA Polymerase that is Defective in RNA Binding and Blocked in the Early Stages of Transcription," Journal of Molecular Biology, 1997, pp. 275-288, vol. 265.
Hénaut, A. and Danchin, A., "Analysis and Predictions from *Escherichia coli* Sequences, or *E. coli* in Silco," *Escherichia coli* and *Salmonella*,1996, pp. 2047-2066, vol. 2, Ch. 114, F. C. Neidhardt, Editor, ASM Press, Washington, DC.
Kopetzki, Erhard et al., "Control of formation of active soluble or inactive insoluble baker's yeast α-glucosidase PI in *Escherichia coli* by induction and growth conditions," Molecular and General Genetics, 1989, pp. 149-155, vol. 216.
Lee, Byungkook and Vasmatzis, George, "Stabilization of protein structures," Current Opinion in Biotechnology, 1997, pp. 423-426, vol. 8.
Ma, Kaiyu et al., "Probing conformational changes in T7 RNA polymerase during initiation and termination by using engineered disulfide linkages," Proceedings of the National Academy of Sciences, Dec. 6, 2005, pp. 17612-17617, vol. 102, No. 49.
Milligan, John F. et al., "Oligoribonucleotide synthesis using T7 RNA polymerase and synthetic DNA templates," Nucleic Acids Research, 1987, pp. 8783-8798, vol. 15, No. 21.
Porath, Jerker et al., "Metal chelate affinity chromatography, a new approach to protein fractionation," Nature, Dec. 18, 1975, pp. 598-599, vol. 258.
Protasevich, I. I. et al., "The studies of cooperative regions in T7 RNA polymerase," FEBS Letters, 1994, pp. 429-432, vol. 349.
Sousa, Rui and Mukherjee, Srabani, "T7 RNA Polymerase," Progress in Nucleic Acid Research and Molecular Biology, 2003, pp. 1-41, vol. 73.
Steitz, Thomas A., "The structural basis of the transition from initiation to elongation phases of transcription, as well as translocation and strand separation, by T7 RNA polymerase," Current Opinion in Structural Biology, 2004, pp. 4-9, vol. 14.
Steitz, Thomas A., "Visualizing polynucleotide polymerase machines at work," The EMBO Journal, 2006, pp. 3458-3468, vol. 25, No. 15.

(Continued)

*Primary Examiner* — Richard Hutson
(74) *Attorney, Agent, or Firm* — Faegre Baker Daniels LLP

(57) ABSTRACT

The present invention provides improved variants of T7 RNA polymerase by introducing novel mutations which lead to improved thermostability of the enzyme. According to the invention, amino acid substitutions at the positions Val426, Ser633, Val650, Thr654, Ala702, Val795, and combinations thereof are advantageous.

11 Claims, No Drawings

(56) References Cited

OTHER PUBLICATIONS

Studier, F. William and Moffatt, Barbara A., "Use of Bacteriophage T7 RNA Polymerase to Direct Selective High-level Expression of Cloned Genes," Journal of Molecular Biology, 1986, pp. 113-130, vol. 189.

Tahirov, Tahir H. et al., "Structure of a T7 RNA Polymerase elongation complex at 2.9 Å resolution," Nature, Nov. 7, 2002, pp. 43-50, vol. 420.

Van Den Brulle, Jan et al., "A novel solid phase technology for high-throughput gene synthesis," Biotechniques, 2008, pp. 340-343, vol. 45, No. 3.

Winter, Greg et al., "Redesigning enzyme structure by site-directed mutagenesis: tyrosyl tRNA synthetase and ATP binding," Nature, Oct. 21, 1982, pp. 756-758, vol. 299.

Yeh, Andrew P. et al., "Rapid and simple protein-stability screens: application to membrane proteins," Acta Crystallographica Section D, 2006, pp. 451-457, vol. D62.

Yin, Y. Whitney and Steitz, Thomas A., "The Structural Mechanism of Translocation and Helicase Activity in T7 RNA Polymerase," Cell, Feb. 6, 2004, pp. 393-404, vol. 116.

\* cited by examiner

SEQUENCE LISTING

<160> NUMBER OF SEQ ID NOS: 54

<210> SEQ ID NO 1
<211> LENGTH: 2655
<212> TYPE: DNA
<213> ORGANISM: Escherichia coli
<220> FEATURE:
<223> OTHER INFORMATION: Phage T7
<220> FEATURE:
<221> NAME/KEY: misc_feature
<222> LOCATION: (1)..(2655)
<223> OTHER INFORMATION: DNA sequence encoding wild-type T7
      DNA-dependent RNA polymerase, including start codon encoding
      N-terminal methionine; corresponding to #1 in Table 3

<400> SEQUENCE: 1
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300

```
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg aaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg tgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                   2655
```

```
-continued

<210> SEQ ID NO 2
<211> LENGTH: 883
<212> TYPE: PRT
<213> ORGANISM: Escherichia coli
<220> FEATURE:
<223> OTHER INFORMATION: Phage T7
<220> FEATURE:
<221> NAME/KEY: misc_feature
<222> LOCATION: (1)..(883)
<223> OTHER INFORMATION: Wild-type T7 DNA-dependent RNA polymerase,
      amino acid sequence including N-terminal methionine; corresponding
      to #1 in Table 3

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335
```

```
Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750
```

-continued

Gly Gln Phe Arg Leu Gln Pro Thr Ile Asn Thr Asn Lys Asp Ser Glu
             755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 3
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the A319S variant of T7
      DNA-dependent RNA polymerase, including start codon encoding
      N-terminal methionine; corresponding to #2 in Table 3

<400> SEQUENCE: 3

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct gaagctaag     480 cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaaagcatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
```

```
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga aacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 4
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: A319S variant of T7 DNA-dependent RNA polymerase, amino acid sequence including N-terminal methionine; corresponding to #2 in Table 3

<400> SEQUENCE: 4

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45
```

```
Ala Arg Phe Arg Lys Met Phe Glu Arg Gln Leu Lys Ala Gly Glu Val
 50                  55                  60

Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                     85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ser Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 5
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the A319V variant of T7
      DNA-dependent RNA polymerase, including start codon encoding
      N-terminal methionine; corresponding to #3 in Table 3

<400> SEQUENCE: 5

| | | |
|---|---|---|
| atgaacacga ttaacatcgc taagaacgac ttctctgaca tcgaactggc tgctatcccg | 60 |
| ttcaacactc tggctgacca ttacggtgag cgtttagctc gcaacagtt ggcccttgag | 120 |
| catgagtctt acgagatggg tgaagcacgc ttccgcaaga tgtttgagcg tcaacttaaa | 180 |
| gctggtgagg ttgcggataa cgctgccgcc aagcctctca tcactaccct actccctaag | 240 |
| atgattgcac gcatcaacga ctggtttgag gaagtgaaag ctaagcgcgg caagcgcccg | 300 |
| acagccttcc agttcctgca agaaatcaag ccggaagccg tagcgtacat caccattaag | 360 |
| accactctgg cttgcctaac cagtgctgac aatacaaccg ttcaggctgt agcaagcgca | 420 |
| atcggtcggg ccattgagga cgaggctcgc ttcggtcgta ccgtgaccct gaagctaag | 480 |
| cacttcaaga aaacgttga ggaacaactc aacagcgcg tagggcacgt ctacaagaaa | 540 |
| gcatttatgc aagttgtcga ggctgacatg ctctctaagg tctactcgg tggcgaggcg | 600 |
| tggtcttcgt ggcataagga agactctatt catgtaggag tacgctgcat cgagatgctc | 660 |
| attgagtcaa ccggaatggt tagcttacac cgccaaaatg ctggcgtagt aggtcaagac | 720 |
| tctgagacta tcgaactcgc acctgaatac gctgaggcta tcgcaacccg tgcaggtgcg | 780 |
| ctggctggca tctctccgat gttccaacct tgcgtagttc ctcctaagcc gtggactggc | 840 |
| attactggtg gtggctattg ggctaacggt cgtcgtcctc tggcgctggt gcgtactcac | 900 |
| agtaagaaag cactgatgcg ctacgaagac gtttacatgc tgaggtgta caaagttatt | 960 |
| aacattgcgc aaaacaccgc atggaaaatc aacaagaaag tcctagcggt cgccaacgta | 1020 |
| atcaccaagt ggaagcattg tccggtcgag acatccctg cgattgagcg tgaagaactc | 1080 |
| ccgatgaaac cggaagacat cgacatgaat cctgaggctc tcaccgcgtg gaaacgtgct | 1140 |
| gccgctgctg tgtaccgcaa ggacaaggct cgcaagtctc gccgtatcag ccttgagttc | 1200 |
| atgcttgagc aagccaataa gtttgctaac cataaggcca tctggttccc ttacaacatg | 1260 |
| gactggcgcg tcgtgttta cgctgtgtca atgttcaacc gcaaggtaa cgatatgacc | 1320 |
| aaaggactgc ttacgctggc gaaaggtaaa ccaatcggta aggaaggtta ctactggctg | 1380 |
| aaaatccacg gtgcaaactg tgcgggtgtc gataaggttc cgttccctga gcgcatcaag | 1440 |
| ttcattgagg aaaaccacga gaacatcatg gcttgcgcta agtctccact ggagaacact | 1500 |
| tggtgggctg agcaagattc tccgttctgc ttccttgcgt tctgctttga gtacgctggg | 1560 |
| gtacagcacc acggcctgag ctataactgc tcccttccgc tggcgtttga cgggtcttgc | 1620 |
| tctggcatcc agcacttctc cgcgatgctc cgagatgagg taggtggtcg cgcggttaac | 1680 |
| ttgcttccta gtgaaaccgt tcaggacatc tacgggattg ttgctaagaa agtcaacgag | 1740 |
| attctacaag cagacgcaat caatgggacc gataacgaag tagttaccgt gaccgatgag | 1800 |
| aacactggtg aaatctctga gaaagtcaag ctgggcacta aggcactggc tggtcaatgg | 1860 |

```
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                      2655
```

<210> SEQ ID NO 6
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: A319V variant of T7 DNA-dependent RNA
      polymerase, amino acid sequence including N-terminal methionine;
      corresponding to #3 in Table 3

<400> SEQUENCE: 6

```
Met Asn Thr Ile Asn Ile Ala Lys Asn Asp Phe Ser Asp Ile Glu Leu
 1               5                  10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

-continued

```
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
    275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Val Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
        340                 345                 350

Pro Ala Ile Glu Arg Glu Glu Leu Pro Met Lys Pro Glu Asp Ile Asp
    355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
        420                 425                 430

Asn Pro Gln Gly Asn Asp Met Thr Lys Gly Leu Leu Thr Leu Ala Lys
    435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
        500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
```

|     |     |     |     |     | 595 |     |     |     |     | 600 |     |     |     |     | 605 |
| --- | --- | --- | --- | --- | --- | --- | --- | --- | --- | --- | --- | --- | --- | --- | --- |

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 7
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the A319P variant of T7
      DNA-dependent RNA polymerase, including start codon encoding
      N-terminal methionine; corresponding to #4 in Table 3

<400> SEQUENCE: 7
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240

```
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa      540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaaccgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgtttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga aacatcatg gcttgcgcta agtctccact ggagaacact     1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg tagtggtcg cgcggttaac     1680 ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcgcttccg tcaacaagtg ctggaagata ccattcagcc agctattgat     1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagataag cgagattgat gcacacaaac aggagtctgg tatcgctcct    2340
aactttgtac acagccaaga cggtagccac cttcgtaaga ctgtagtgtg gcacacgag     2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
```

-continued

```
atgccagcac ttccggctaa aggtaacttg aacctccgtg acatcttaga gtcggacttc    2640
gcgttcgcgt aataa    2655
```

<210> SEQ ID NO 8
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: A319P variant of T7 DNA-dependent RNA
      polymerase, amino acid sequence including N-terminal methionine;
      corresponding to #4 in Table 3

<400> SEQUENCE: 8

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Pro Ile
```

```
                305                 310                 315                 320
Asn Ile Ala Gln Asn Thr Ala Trp Lys Ile Asn Lys Lys Val Leu Ala
                    325                 330                 335

Val Ala Asn Val Ile Thr Lys Trp Lys His Cys Pro Val Glu Asp Ile
                    340                 345                 350

Pro Ala Ile Glu Arg Glu Glu Leu Pro Met Lys Pro Glu Asp Ile Asp
                    355                 360                 365

Met Asn Pro Glu Ala Leu Thr Ala Trp Lys Arg Ala Ala Ala Val
            370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                    405                 410                 415

Pro Tyr Asn Met Asp Trp Arg Gly Arg Val Tyr Ala Val Ser Met Phe
                    420                 425                 430

Asn Pro Gln Gly Asn Asp Met Thr Lys Gly Leu Leu Thr Leu Ala Lys
                    435                 440                 445

Gly Lys Pro Ile Gly Lys Glu Gly Tyr Tyr Trp Leu Lys Ile His Gly
                    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                    485                 490                 495

Leu Glu Asn Thr Trp Trp Ala Glu Gln Asp Ser Pro Phe Cys Phe Leu
                    500                 505                 510

Ala Phe Cys Phe Glu Tyr Ala Gly Val Gln His His Gly Leu Ser Tyr
                    515                 520                 525

Asn Cys Ser Leu Pro Leu Ala Phe Asp Gly Ser Cys Ser Gly Ile Gln
                    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                    565                 570                 575

Lys Val Asn Glu Ile Leu Gln Ala Asp Ala Ile Asn Gly Thr Asp Asn
                    580                 585                 590

Glu Val Val Thr Val Thr Asp Glu Asn Thr Gly Glu Ile Ser Glu Lys
                    595                 600                 605

Val Lys Leu Gly Thr Lys Ala Leu Ala Gly Gln Trp Leu Ala Tyr Gly
                    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                    645                 650                 655

Pro Ala Ile Asp Ser Gly Lys Gly Leu Met Phe Thr Gln Pro Asn Gln
                    660                 665                 670

Ala Ala Gly Tyr Met Ala Lys Leu Ile Trp Glu Ser Val Ser Val Thr
                    675                 680                 685

Val Val Ala Ala Val Glu Ala Met Asn Trp Leu Lys Ser Ala Ala Lys
                    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                    725                 730                 735
```

-continued

```
Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 9
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L variant of T7
      DNA-dependent RNA polymerase, including start codon encoding
      N-terminal methionine; corresponding to #5 in Table 3

<400> SEQUENCE: 9
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaaacgttga ggaacaactc aacaagcgcg tagggcacgt ctacaagaaa     540
gcatttatgc aagttgtcga ggctgacatg ctctctaagg tctactcgg tggcgaggcg      600 tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960
```

-continued

```
aacattgcgc aaaacaccgc atggaaaatc aacaagaaag tcctagcggt cgccaacgta  1020
atcaccaagt ggaagcattg tccggtcgag acatccctg cgattgagcg tgaagaactc  1080
ccgatgaaac cggaagacat cgacatgaat cctgaggctc tcaccgcgtg aaacgtgct  1140 gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg tcgtctgta cgctgtgtca atgttcaacc cgcaaggtaa cgatatgacc  1320
aaaggactgc ttacgctggc gaaaggtaaa ccaatcggta aggaaggtta ctactggctg  1380
aaaatccacg gtgcaaactg tgcgggtgtc gataaggttc cgttccctga gcgcatcaag  1440
ttcattgagg aaaaccacga gaacatcatg gcttgcgcta agtctccact ggagaacact  1500
tggtgggctg agcaagattc tccgttctgc ttccttgcgt tctgctttga gtacgctggg  1560
gtacagcacc acggcctgag ctataactgc tcccttccgc tggcgtttga cgggtcttgc  1620
tctggcatcc agcacttctc cgcgatgctc cgagatgagg taggtggtcg cgcggttaac  1680
ttgcttccta gtgaaaccgt tcaggacatc tacgggattg ttgctaagaa agtcaacgag  1740
attctacaag cagacgcaat caatgggacc gataacgaag tagttaccgt gaccgatgag  1800
aacactggtg aaatctctga aaagtcaag ctgggcacta aggcactggc tggtcaatgg  1860
ctggcttacg gtgttactcg cagtgtgact aagcgttcag tcatgacgct ggcttacggg  1920
tccaaagagt tcggcttccg tcaacaagtg ctggaagata ccattcagcc agctattgat  1980
tccggcaagg gtctgatgtt cactcagccg aatcaggctg ctggatacat ggctaagctg  2040
atttgggaat ctgtgagcgt gacggtggta gctgcggttg aagcaatgaa ctggcttaag  2100
tctgctgcta agctgctggc tgctgaggtc aaagataaga gactggaga gattcttcgc  2160 aagcgttgcg ctgtgcattg ggtaactcct gatggttccc ctgtgtggca ggaatacaag  2220
aagcctattc agacgcgctt gaacctgatg ttcctcggtc agttccgctt acagcctacc  2280
attaacacca caaagatag cgagattgat gcacacaaac aggagtctgg tatcgctcct  2340
aactttgtac acagccaaga cggtagccac cttcgtaaga ctgtagtgtg ggcacacgag  2400
aagtacggaa tcgaatcttt tgcactgatt cacgactcct tcggtaccat tccggctgac  2460
gctgcgaacc tgttcaaagc agtgcgcgaa actatggttg acacatatga gtcttgtgat  2520
gtactggctg atttctacga ccagttcgct gaccagttgc acgagtctca attggacaaa  2580
atgccagcac ttccggctaa aggtaacttg aacctccgtg acatcttaga gtcggacttc  2640
gcgttcgcgt aataa                                                    2655
```

<210> SEQ ID NO 10
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L variant of T7 DNA-dependent RNA polymerase, amino acid sequence including N-terminal methionine; corresponding to #5 in Table 3

<400> SEQUENCE: 10

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu

```
                20                  25                  30
Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445
```

```
Gly Lys Pro Ile Gly Lys Glu Gly Tyr Tyr Trp Leu Lys Ile His Gly
    450             455                 460

Ala Asn Cys Ala Gly Val Asp Lys Val Pro Phe Pro Glu Arg Ile Lys
465             470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860
```

```
Pro Ala Lys Gly Asn Leu Asn Leu Arg Asp Ile Leu Glu Ser Asp Phe
865                 870                 875                 880

Ala Phe Ala

<210> SEQ ID NO 11
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426I variant of T7
      DNA-dependent RNA polymerase, including start codon encoding
      N-terminal methionine; corresponding to #6 in Table 3

<400> SEQUENCE: 11
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct gaagctaag      480 cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtatcta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta gtctccact ggagaacact    1500 tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
```

-continued

```
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag   2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

```
<210> SEQ ID NO 12
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: V426I variant of T7 DNA-dependent RNA
      polymerase, amino acid sequence including N-terminal methionine;
      corresponding to #6 in Table 3

<400> SEQUENCE: 12

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160
```

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Ile Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

```
Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 13
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426F variant of T7
      DNA-dependent RNA polymerase, including start codon encoding
      N-terminal methionine; corresponding to #7 in Table 3

<400> SEQUENCE: 13
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
```

```
catgagtctt acgagatggg tgaagcacgc ttccgcaaga tgtttgagcg tcaacttaaa      180
gctggtgagg ttgcggataa cgctgccgcc aagcctctca tcactaccct actccctaag      240
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggc ccattgagga cgaggctcgc ttcggtcgta ccgtgaccct tgaagctaag      480
cacttcaaga aaacgttga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtttcta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga aacatcatg gcttgcgcta agtctccact ggagaacact     1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga aaagtcaag ctgggcacta aggcactggc tggtcaatgg     1860
ctggcttacg gtgttactcg cagtgtgact aagcgttcag tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta agctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctgtagtgtg gcacacgag     2400
aagtacggaa tcgaatcttt tgcactgatt cacgactcct tcggtaccat tccggctgac     2460
```

```
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 14
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: V426F variant of T7 DNA-dependent RNA
      polymerase, amino acid sequence including N-terminal methionine;
      corresponding to #7 in Table 3

<400> SEQUENCE: 14

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285
```

-continued

```
Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Phe Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
```

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 15
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the S633V variant of T7
      DNA-dependent RNA polymerase, including start codon encoding
      N-terminal methionine; corresponding to #10 in Table 3

<400> SEQUENCE: 15
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840

```
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgtgttg tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga gactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 16  
<211> LENGTH: 883  
<212> TYPE: PRT  
<213> ORGANISM: Artificial Sequence  
<220> FEATURE:  
<223> OTHER INFORMATION: Description of Artificial Sequence: Synthetic variant polypeptide  
<220> FEATURE:  
<221> NAME/KEY: misc_feature  
<222> LOCATION: (1)..(883)  
<223> OTHER INFORMATION: S633V variant of T7 DNA-dependent RNA polymerase, amino acid sequence including N-terminal methionine; corresponding to #10 in Table 3

<400> SEQUENCE: 16

-continued

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
    195                 200                 205

Ser Ile His Val Gly Val Arg Cys Ile Glu Met Leu Ile Glu Ser Thr
210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
```

-continued

```
                420             425             430
Asn Pro Gln Gly Asn Asp Met Thr Lys Gly Leu Leu Thr Leu Ala Lys
            435             440             445
Gly Lys Pro Ile Gly Lys Glu Gly Tyr Tyr Trp Leu Lys Ile His Gly
            450             455             460
Ala Asn Cys Ala Gly Val Asp Lys Val Pro Phe Pro Glu Arg Ile Lys
465             470             475             480
Phe Ile Glu Glu Asn His Glu Asn Ile Met Ala Cys Ala Lys Ser Pro
                485             490             495
Leu Glu Asn Thr Trp Trp Ala Glu Gln Asp Ser Pro Phe Cys Phe Leu
            500             505             510
Ala Phe Cys Phe Glu Tyr Ala Gly Val Gln His Gly Leu Ser Tyr
            515             520             525
Asn Cys Ser Leu Pro Leu Ala Phe Asp Gly Ser Cys Ser Gly Ile Gln
            530             535             540
His Phe Ser Ala Met Leu Arg Asp Glu Val Gly Gly Arg Ala Val Asn
545             550             555             560
Leu Leu Pro Ser Glu Thr Val Gln Asp Ile Tyr Gly Ile Val Ala Lys
            565             570             575
Lys Val Asn Glu Ile Leu Gln Ala Asp Ala Ile Asn Gly Thr Asp Asn
            580             585             590
Glu Val Val Thr Val Thr Asp Glu Asn Thr Gly Glu Ile Ser Glu Lys
            595             600             605
Val Lys Leu Gly Thr Lys Ala Leu Ala Gly Gln Trp Leu Ala Tyr Gly
            610             615             620
Val Thr Arg Ser Val Thr Lys Arg Val Val Met Thr Leu Ala Tyr Gly
625             630             635             640
Ser Lys Glu Phe Gly Phe Arg Gln Gln Val Leu Glu Asp Thr Ile Gln
            645             650             655
Pro Ala Ile Asp Ser Gly Lys Gly Leu Met Phe Thr Gln Pro Asn Gln
            660             665             670
Ala Ala Gly Tyr Met Ala Lys Leu Ile Trp Glu Ser Val Ser Val Thr
            675             680             685
Val Val Ala Ala Val Glu Ala Met Asn Trp Leu Lys Ser Ala Ala Lys
            690             695             700
Leu Leu Ala Ala Glu Val Lys Asp Lys Thr Gly Glu Ile Leu Arg
705             710             715             720
Lys Arg Cys Ala Val His Trp Val Thr Pro Asp Gly Phe Pro Val Trp
            725             730             735
Gln Glu Tyr Lys Lys Pro Ile Gln Thr Arg Leu Asn Leu Met Phe Leu
            740             745             750
Gly Gln Phe Arg Leu Gln Pro Thr Ile Asn Thr Asn Lys Asp Ser Glu
            755             760             765
Ile Asp Ala His Lys Gln Glu Ser Gly Ile Ala Pro Asn Phe Val His
            770             775             780
Ser Gln Asp Gly Ser His Leu Arg Lys Thr Val Val Trp Ala His Glu
785             790             795             800
Lys Tyr Gly Ile Glu Ser Phe Ala Leu Ile His Asp Ser Phe Gly Thr
            805             810             815
Ile Pro Ala Asp Ala Ala Asn Leu Phe Lys Ala Val Arg Glu Thr Met
            820             825             830
Val Asp Thr Tyr Glu Ser Cys Asp Val Leu Ala Asp Phe Tyr Asp Gln
            835             840             845
```

```
Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 17
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the S633L variant of T7
      DNA-dependent RNA polymerase, including start codon encoding
      N-terminal methionine; corresponding to #11 in Table 3

<400> SEQUENCE: 17
atgaacacga ttaacatcgc taagaacgac ttctctgaca tcgaactggc tgctatcccg     60
ttcaacactc tggctgacca ttacggtgag cgtttagctc gcaacagtt ggcccttgag    120 catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct gaagctaag    480 cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg aaacgtgct   1140 gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctc agcaagattc tccgttctgc ttccttgcgt tctgctttga gtacgctggg   1560
gtacagcacc acggcctgag ctataactgc tcccttccgc tggcgtttga cgggtcttgc   1620
```

```
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg     1860
ctggcttacg gtgttactcg cagtgtgact aagcgtctgg tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 18
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: S633L variant of T7 DNA-dependent RNA
      polymerase, amino acid sequence including N-terminal methionine;
      corresponding to #11 in Table 3

<400> SEQUENCE: 18

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
```

```
                130                 135                 140
Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
    275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560
```

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Leu Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 19
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the S633M variant of T7
      DNA-dependent RNA polymerase, including start codon encoding
      N-terminal methionine; corresponding to #12 in Table 3

<400> SEQUENCE: 19

```
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggg ccattgagga cgaggctcgc ttcggtcgta ccgtgaccct gaagctaag   480 cacttcaaga aaacgttga ggaacaactc aacaagcgcg tagggcacgt ctacaagaaa   540
gcatttatgc aagttgtcga ggctgacatg ctctctaagg gtctactcgg tggcgaggcg   600
tggtcttcgt ggcataagga agactctatt catgtaggag tacgctgcat cgagatgctc   660
attgagtcaa ccggaatggt tagcttacac cgccaaaatg ctggcgtagt aggtcaagac   720
tctgagacta tcgaactcgc acctgaatac gctgaggcta tcgcaacccg tgcaggtgcg   780
ctggctggca tctctccgat gttccaacct tgcgtagttc ctcctaagcc gtggactggc   840
attactggtg gtggctattg gctaacggt cgtcgtcctc tggcgctggt gcgtactcac   900
agtaagaaag cactgatgcg ctacgaagac gtttacatgc tgaggtgta caaagcgatt   960 aacattgcgc aaaacaccgc atggaaaatc aacaagaaag tcctagcggt cgccaacgta  1020
atcaccaagt ggaagcattg tccggtcgag gacatccctg cgattgagcg tgaagaactc  1080
ccgatgaaac cggaagacat cgacatgaat cctgaggctc tcaccgcgtg gaaacgtgct  1140
gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg tcgtgtttta cgctgtgtca atgttcaacc cgcaaggtaa cgatatgacc  1320
aaaggactgc ttacgctggc gaaaggtaaa ccaatcggta aggaaggtta ctactggctg  1380
aaaatccacg gtgcaaactg tgcgggtgtc gataaggttc cgttccctga gcgcatcaag  1440
ttcattgagg aaaaccacga gaacatcatg gcttgcgcta agtctccact ggagaacact  1500
tggtgggctg agcaagattc tccgttctgc ttccttgcgt tctgctttga gtacgctggg  1560
gtacagcacc acggcctgag ctataactgc tcccttccgc tggcgtttga cgggtcttgc  1620
tctggcatcc agcacttctc cgcgatgctc cgagatgagg taggtggtcg cgcggttaac  1680
ttgcttccta gtgaaaccgt tcaggacatc tacgggattg ttgctaagaa agtcaacgag  1740
attctacaag cagacgcaat caatgggacc gataacgaag tagttaccgt gaccgatgag  1800
aacactggtg aaatctctga aaagtcaag ctgggcacta aggcactggc tggtcaatgg  1860
ctggcttacg gtgttactcg cagtgtgact aagcgtatgg tcatgacgct ggcttacggg  1920
tccaaagagt tcggcttccg tcaacaagtg ctggaagata ccattcagcc agctattgat  1980
tccggcaagg gtctgatgtt cactcagccg aatcaggctg ctggatacat ggctaagctg  2040
atttgggaat ctgtgagcgt gacggtggta gctgcggttg aagcaatgaa ctggcttaag  2100
tctgctgcta agctgctggc tgctgaggtc aaagataaga agactggaga gattcttcgc  2160
aagcgttgcg ctgtgcattg ggtaactcct gatggtttcc ctgtgtggca ggaatacaag  2220
aagcctattc agcgcgcgctt gaacctgatg ttcctcggtc agttccgctt acagcctacc  2280
attaacacca acaaagatag cgagattgat gcacacaaac aggagtctgg tatcgctcct  2340
```

```
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 20
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: S633M variant of T7 DNA-dependent RNA
      polymerase, amino acid sequence including N-terminal methionine;
      corresponding to #12 in Table 3

<400> SEQUENCE: 20

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270
```

```
Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
        610                 615                 620

Val Thr Arg Ser Val Thr Lys Arg Met Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
        675                 680                 685
```

```
Val Val Ala Ala Val Glu Ala Met Asn Trp Leu Lys Ser Ala Ala Lys
    690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 21
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V650L variant of T7
      DNA-dependent RNA polymerase, including start codon encoding
      N-terminal methionine; corresponding to #13 in Table 3

<400> SEQUENCE: 21
atgaacacga ttaacatcgc taagaacgac ttctctgaca tcgaactggc tgctatcccg     60
ttcaacactc tggctgacca ttacggtgag cgtttagctc gcaacagtt ggcccttgag    120 catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
```

```
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtgtttta cgctgtgtca atgttcaacc cgcaaggtaa cgatatgacc     1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga gaacatcatg gcttgcgcta agtctccact ggagaacact     1500
tggtgggctg agcaagattc tccgttctgc ttccttgcgt tctgctttga gtacgctggg     1560
gtacagcacc acgcctgag ctataactgc tcccttccgc tggcgtttga cgggtcttgc      1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga gaaagtcaag ctgggcacta aggcactggc tggtcaatgg     1860
ctggcttacg gtgttactcg cagtgtgact aagcgttcag tcatgacgct ggcttacggg     1920
tccaaagagt tcggcttccg tcaacaactg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgctgcta agctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca caaagatag cgagattgat gcacacaaac aggagtctgg tatcgctcct      2340
aactttgtac acagccaaga cggtagccac cttcgtaaga ctgtagtgtg ggcacacgag     2400
aagtacggaa tcgaatcttt tgcactgatt cacgactcct tcggtaccat tccggctgac     2460
gctgcgaacc tgttcaaagc agtgcgcgaa actatggttg acacatatga gtcttgtgat     2520
gtactggctg atttctacga ccagttcgct gaccagttgc acgagtctca attggacaaa     2580
atgccagcac ttccggctaa aggtaacttg aacctccgtg acatcttaga gtcggacttc     2640
gcgttcgcgt aataa                                                     2655
```

<210> SEQ ID NO 22
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V650L variant of T7 DNA-dependent RNA polymerase, amino acid sequence including N-terminal methionine;

corresponding to #13 in Table 3

<400> SEQUENCE: 22

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Val Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
            370                 375                 380

Tyr Arg Lys Asp Lys Ala Arg Lys Ser Arg Arg Ile Ser Leu Glu Phe
385                 390                 395                 400
```

```
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala Tyr Gly
    610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Leu Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
    690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
```

```
                820                 825                 830
Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 23
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the T654L variant of T7
      DNA-dependent RNA polymerase, including start codon encoding
      N-terminal methionine; corresponding to #14 in Table 3

<400> SEQUENCE: 23
atgaacacga ttaacatcgc taagaacgac ttctctgaca tcgaactggc tgctatcccg      60
ttcaacactc tggctgacca ttacggtgag cgtttagctc gcaacagtt ggcccttgag     120 catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct gaagctaag      480 cacttcaaga aaacgttga ggaacaactc aacaagcgcg tagggcacgt ctacaagaaa     540
gcatttatgc aagttgtcga ggctgacatg ctctctaagg tctactcgg tggcgaggcg     600 tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg gctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
```

-continued

```
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg     1860
ctggcttacg gtgttactcg cagtgtgact aagcgttcag tcatgacgct ggcttacggg    1920
tccaaagagt tcggcttccg tcaacaagtg ctggaagatc tgattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg gcacacgag    2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa    2655
```

<210> SEQ ID NO 24
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: T654L variant of T7 DNA-dependent RNA
      polymerase, amino acid sequence including N-terminal methionine;
      corresponding to #14 in Table 3

<400> SEQUENCE: 24

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110
```

```
Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Glu Ala Asp Met Leu Ser
            180                 185                 190

Lys Gly Leu Leu Gly Gly Glu Ala Trp Ser Ser Trp His Lys Glu Asp
    195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
```

```
                530                 535                 540
His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Leu Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 25
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the A702V variant of T7
```

DNA-dependent RNA polymerase, including start codon encoding
N-terminal methionine; corresponding to #15 in Table 3

<400> SEQUENCE: 25

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta ccgtgaccct gaagctaag      480
cacttcaaga aaacgttga  ggaacaactc aacaagcgcg tagggcacgt ctacaagaaa     540
gcatttatgc aagttgtcga ggctgacatg ctctctaagg gtctactcgg tgcgaggcg      600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg gctaacggt  cgtcgtcctc tggcgctggt gcgtactcac     900
agtaagaaag cactgatgcg ctacgaagac gtttacatgc tgaggtgta  caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta gtctccact  ggagaacact    1500
tggtgggctg agcaagattc tccgttctgc ttccttgcgt tctgctttga gtacgctggg    1560
gtacagcacc acggctgag  ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag  ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctc tggatacat  ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
```

-continued

```
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 26
<211> LENGTH: 883
<212> TYPE: PRT
<213> ORGANISM: Artificial Sequence
<220> FEATURE:
<223> OTHER INFORMATION: Description of Artificial Sequence: Synthetic
    variant polypeptide
<220> FEATURE:
<221> NAME/KEY: misc_feature
<222> LOCATION: (1)..(883)
<223> OTHER INFORMATION: A702V variant of T7 DNA-dependent RNA
    polymerase, amino acid sequence including N-terminal methionine;
    corresponding to #15 in Table 3

<400> SEQUENCE: 26

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
```

-continued

```
            245                 250                 255
Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280             285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670
```

```
Ala Ala Gly Tyr Met Ala Lys Leu Ile Trp Glu Ser Val Ser Val Thr
            675                 680                 685
Val Val Ala Ala Val Glu Ala Met Asn Trp Leu Lys Ser Val Ala Lys
    690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 27
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the L705I variant of T7
      DNA-dependent RNA polymerase, including start codon encoding
      N-terminal methionine; corresponding to #16 in Table 3

<400> SEQUENCE: 27
atgaacacga ttaacatcgc taagaacgac ttctctgaca tcgaactggc tgctatcccg      60
ttcaacactc tggctgacca ttacggtgag cgtttagctc gcaacagtt ggcccttgag      120 catgagtctt acgagatggg tgaagcacgc ttccgcaaga tgtttgagcg tcaacttaaa     180
gctggtgagg ttgcggataa cgctgccgcc aagcctctca tcactaccct actccctaag    240
atgattgcac gcatcaacga ctggtttgag gaagtgaaag ctaagcgcgg caagcgcccg     300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
```

```
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc    1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta gtctccact ggagaacact    1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agatcctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655

<210> SEQ ID NO 28
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
```

<220> NAME/KEY: misc_feature
<222> LOCATION: (1)..(883)
<223> OTHER INFORMATION: L705I variant of T7 DNA-dependent RNA
      polymerase, amino acid sequence including N-terminal methionine;
      corresponding to #16 in Table 3

<400> SEQUENCE: 28

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380
```

```
Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Ile Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800
```

Lys Tyr Gly Ile Glu Ser Phe Ala Leu Ile His Asp Ser Phe Gly Thr
                    805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 29
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V795I variant of T7
      DNA-dependent RNA polymerase, including start codon encoding
      N-terminal methionine; corresponding to #18 in Table 3

<400> SEQUENCE: 29

```
atgaacacga ttaacatcgc taagaacgac ttctctgaca tcgaactggc tgctatcccg      60
ttcaacactc tggctgacca ttacggtgag cgtttagctc gcaacagtt ggcccttgag      120
catgagtctt acgagatggg tgaagcacgc ttccgcaaga tgtttgagcg tcaacttaaa      180
gctggtgagg ttgcggataa cgctgccgcc aagcctctca tcactaccct actccctaag      240
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggg ccattgagga cgaggctcgc ttcggtcgta ccgtgacct tgaagctaag      480
cacttcaaga aaaacgttga ggaacaactc aacaagcgcg tagggcacgt ctacaagaaa      540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc tgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg gtcgtgtttta cgctgtgtca atgttcaacc cgcaaggtaa cgatatgacc     1320
aaaggactgc ttacgctggc gaaaggtaaa ccaatcggta aggaaggtta ctactggctg     1380
```

```
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctatcgtgtg gcacacgag   2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 30
<211> LENGTH: 883
<212> TYPE: PRT
<213> ORGANISM: Artificial Sequence
<220> FEATURE:
<223> OTHER INFORMATION: Description of Artificial Sequence: Synthetic
    variant polypeptide
<220> FEATURE:
<221> NAME/KEY: misc_feature
<222> LOCATION: (1)..(883)
<223> OTHER INFORMATION: V795I variant of T7 DNA-dependent RNA
    polymerase, amino acid sequence including N-terminal methionine;
    corresponding to #18 in Table 3

<400> SEQUENCE: 30

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95
```

-continued

```
Gly Lys Arg Pro Thr Ala Phe Gln Phe Leu Gln Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510
```

Ala Phe Cys Phe Glu Tyr Ala Gly Val Gln His His Gly Leu Ser Tyr
515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 31
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide <220> FEATURE:
<221> NAME/KEY: misc_feature
<222> LOCATION: (1)..(2655)
<223> OTHER INFORMATION: DNA sequence encoding the L809F variant of T7
      DNA-dependent RNA polymerase, including start codon encoding
      N-terminal methionine; corresponding to #19 in Table 3

<400> SEQUENCE: 31

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | tgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | tcgtgtttta | cgctgtgtca | atgttcaacc | cgcaaggtaa | cgatatgacc | 1320 |
| aaaggactgc | ttacgctggc | gaaagtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | gaacatcatg | gcttgcgcta | gtctccact | ggagaacact | 1500 |
| tggtgggctg | agcaagattc | tccgttctgc | ttccttgcgt | tctgctttga | gtacgctggg | 1560 |
| gtacagcacc | acggcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattc | ttgctaagaa | agtcaacgag | 1740 |
| attctacaag | cagacgcaat | caatgggacc | gataacgaag | tagttaccgt | gaccgatgag | 1800 |
| aacactggtg | aaatctctga | aaagtcaag | ctgggcacta | aggcactggc | tggtcaatgg | 1860 |
| ctggcttacg | gtgttactcg | cagtgtgact | aagcgttcag | tcatgacgct | ggcttacggg | 1920 |
| tccaaagagt | tcggcttccg | tcaacaagtg | ctggaagata | ccattcagcc | agctattgat | 1980 |
| tccggcaagg | gtctgatgtt | cactcagccg | aatcaggctg | ctggatacat | ggctaagctg | 2040 |
| atttgggaat | ctgtgagcgt | gacggtggta | gctgcggttg | aagcaatgaa | ctggcttaag | 2100 |

-continued

```
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcattcatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 32
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: L809F variant of T7 DNA-dependent RNA
      polymerase, amino acid sequence including N-terminal methionine;
      corresponding to #19 in Table 3

<400> SEQUENCE: 32

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

-continued

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
        260                 265                 270

Val Pro Pro Lys Pro Trp Thr Gly Ile Thr Gly Gly Tyr Trp Ala
    275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
```

```
                    645                 650                 655
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Phe Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 33
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the F814W variant of T7
      DNA-dependent RNA polymerase, including start codon encoding
      N-terminal methionine; corresponding to #20 in Table 3

<400> SEQUENCE: 33
atgaacacga ttaacatcgc taagaacgac ttctctgaca tcgaactggc tgctatcccg       60
ttcaacactc tggctgacca ttacggtgag cgtttagctc gcgaacagtt ggcccttgag      120
catgagtctt acgagatggg tgaagcacgc ttccgcaaga tgtttgagcg tcaacttaaa      180
gctggtgagg ttgcggataa cgctgccgcc aagcctctca tcactaccct actcccgaag      240
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggg ccattgagga cgaggctcgc ttcggtcgta tccgtgacct tgaagctaag      480
```

```
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtgtttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta gtctccact ggagaacact   1500 tggtgggctg agcaagattc tccgttctgc ttccttgcgt tctgctttga gtacgctggg   1560
gtacagcacc acgcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag    2400 aagtacggaa tcgaatcttt tgcactgatt cacgactcct ggggtaccat tccggctgac   2460
gctgcgaacc tgttcaaagc agtgcgcgaa actatggttc acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                   2655
```

<210> SEQ ID NO 34
<211> LENGTH: 883
<212> TYPE: PRT
<213> ORGANISM: Artificial Sequence -continued

```
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: F814W variant of T7 DNA-dependent RNA
      polymerase, amino acid sequence including N-terminal methionine;
      corresponding to #20 in Table 3

<400> SEQUENCE: 34

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
```

-continued

```
              355                 360                 365
Met Asn Pro Glu Ala Leu Thr Ala Trp Lys Arg Ala Ala Ala Val
              370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                    405                 410                 415
Pro Tyr Asn Met Asp Trp Arg Gly Arg Val Tyr Ala Val Ser Met Phe
                420                 425                 430
Asn Pro Gln Gly Asn Asp Met Thr Lys Gly Leu Leu Thr Leu Ala Lys
                    435                 440                 445
Gly Lys Pro Ile Gly Lys Glu Gly Tyr Tyr Trp Leu Lys Ile His Gly
                450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                    485                 490                 495
Leu Glu Asn Thr Trp Trp Ala Glu Gln Asp Ser Pro Phe Cys Phe Leu
                500                 505                 510
Ala Phe Cys Phe Glu Tyr Ala Gly Val Gln His His Gly Leu Ser Tyr
                515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
                580                 585                 590
Glu Val Val Thr Val Thr Asp Glu Asn Thr Gly Glu Ile Ser Glu Lys
                595                 600                 605
Val Lys Leu Gly Thr Lys Ala Leu Ala Gly Gln Trp Leu Ala Tyr Gly
                610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                    645                 650                 655
Pro Ala Ile Asp Ser Gly Lys Gly Leu Met Phe Thr Gln Pro Asn Gln
                660                 665                 670
Ala Ala Gly Tyr Met Ala Lys Leu Ile Trp Glu Ser Val Ser Val Thr
                    675                 680                 685
Val Val Ala Ala Val Glu Ala Met Asn Trp Leu Lys Ser Ala Ala Lys
                690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                    725                 730                 735
Gln Glu Tyr Lys Lys Pro Ile Gln Thr Arg Leu Asn Leu Met Phe Leu
                740                 745                 750
Gly Gln Phe Arg Leu Gln Pro Thr Ile Asn Thr Asn Lys Asp Ser Glu
                755                 760                 765
Ile Asp Ala His Lys Gln Glu Ser Gly Ile Ala Pro Asn Phe Val His
                770                 775                 780
```

```
Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Trp Gly Thr
            805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
                850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 35
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the M861W variant of T7
      DNA-dependent RNA polymerase, including start codon encoding
      N-terminal methionine; corresponding to #21 in Table 3

<400> SEQUENCE: 35
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct gaagctaag    480 cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggtc gtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
```

```
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta gtctccact ggagaacact   1500 tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
tggccagcac ttccggctaa aggtaacttg aacctccgtg acatcttaga gtcggacttc   2640
gcgttcgcgt aataa                                                   2655
```

<210> SEQ ID NO 36
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: M861W variant of T7 DNA-dependent RNA
      polymerase, amino acid sequence including N-terminal methionine;
      corresponding to #21 in Table 3

<400> SEQUENCE: 36

```
Met Asn Thr Ile Asn Ile Ala Lys Asn Asp Phe Ser Asp Ile Glu Leu
  1               5                  10                  15

Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Ala Lys Pro Leu Ile Thr Thr Leu Leu Pro Lys
```

```
                65                  70                  75                  80
        Met Ile Ala Arg Ile Asn Asp Trp Phe Glu Glu Val Lys Ala Lys Arg
                        85                  90                  95
        Gly Lys Arg Pro Thr Ala Phe Gln Phe Leu Gln Glu Ile Lys Pro Glu
                    100                 105                 110
        Ala Val Ala Tyr Ile Thr Ile Lys Thr Thr Leu Ala Cys Leu Thr Ser
                    115                 120                 125
        Ala Asp Asn Thr Thr Val Gln Ala Val Ala Ser Ala Ile Gly Arg Ala
                130                 135                 140
        Ile Glu Asp Glu Ala Arg Phe Gly Arg Ile Arg Asp Leu Glu Ala Lys
        145                 150                 155                 160
        His Phe Lys Lys Asn Val Glu Gln Leu Asn Lys Arg Val Gly His
                        165                 170                 175
        Val Tyr Lys Lys Ala Phe Met Gln Val Glu Ala Asp Met Leu Ser
                    180                 185                 190
        Lys Gly Leu Leu Gly Gly Glu Ala Trp Ser Ser Trp His Lys Glu Asp
                    195                 200                 205
        Ser Ile His Val Gly Val Arg Cys Ile Glu Met Leu Ile Glu Ser Thr
                210                 215                 220
        Gly Met Val Ser Leu His Arg Gln Asn Ala Gly Val Val Gly Gln Asp
        225                 230                 235                 240
        Ser Glu Thr Ile Glu Leu Ala Pro Glu Tyr Ala Glu Ala Ile Ala Thr
                        245                 250                 255
        Arg Ala Gly Ala Leu Ala Gly Ile Ser Pro Met Phe Gln Pro Cys Val
                    260                 265                 270
        Val Pro Pro Lys Pro Trp Thr Gly Ile Thr Gly Gly Tyr Trp Ala
                    275                 280                 285
        Asn Gly Arg Arg Pro Leu Ala Leu Val Arg Thr His Ser Lys Lys Ala
                290                 295                 300
        Leu Met Arg Tyr Glu Asp Val Tyr Met Pro Glu Val Tyr Lys Ala Ile
        305                 310                 315                 320
        Asn Ile Ala Gln Asn Thr Ala Trp Lys Ile Asn Lys Lys Val Leu Ala
                        325                 330                 335
        Val Ala Asn Val Ile Thr Lys Trp Lys His Cys Pro Val Glu Asp Ile
                    340                 345                 350
        Pro Ala Ile Glu Arg Glu Leu Pro Met Lys Pro Glu Asp Ile Asp
                    355                 360                 365
        Met Asn Pro Glu Ala Leu Thr Ala Trp Lys Arg Ala Ala Ala Val
                370                 375                 380
        Tyr Arg Lys Asp Lys Ala Arg Lys Ser Arg Arg Ile Ser Leu Glu Phe
        385                 390                 395                 400
        Met Leu Glu Gln Ala Asn Lys Phe Ala Asn His Lys Ala Ile Trp Phe
                        405                 410                 415
        Pro Tyr Asn Met Asp Trp Arg Gly Arg Val Tyr Ala Val Ser Met Phe
                    420                 425                 430
        Asn Pro Gln Gly Asn Asp Met Thr Lys Gly Leu Leu Thr Leu Ala Lys
                    435                 440                 445
        Gly Lys Pro Ile Gly Lys Glu Gly Tyr Tyr Trp Leu Lys Ile His Gly
                450                 455                 460
        Ala Asn Cys Ala Gly Val Asp Lys Val Pro Phe Pro Glu Arg Ile Lys
        465                 470                 475                 480
        Phe Ile Glu Glu Asn His Glu Asn Ile Met Ala Cys Ala Lys Ser Pro
                        485                 490                 495
```

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Trp Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 37
<211> LENGTH: 2655
<212> TYPE: DNA

<213> ORGANISM: Artificial Sequence
<220> FEATURE:
<223> OTHER INFORMATION: Description of Artificial Sequence: Synthetic coding polynucleotide
<220> FEATURE:
<221> NAME/KEY: misc_feature
<222> LOCATION: (1)..(2655)
<223> OTHER INFORMATION: DNA sequence encoding the A702V, V795I variant (double mutant) of T7 DNA-dependent RNA polymerase, including start codon encoding N-terminal methionine; corresponding to #22 in Table 3

<400> SEQUENCE: 37

```
atgaacacga ttaacatcgc taagaacgac ttctctgaca tcgaactggc tgctatcccg    60
ttcaacactc tggctgacca ttacggtgag cgtttagctc gcgaacagtt ggcccttgag   120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggc ccattgagga cgaggctcgc ttcggtcgta ccgtgaccct tgaagctaag   480
cacttcaaga aaacgttga ggaacaactc aacaagcgcg tagggcacgt ctacaagaaa   540
gcatttatgc aagttgtcga ggctgacatg ctctctaagg gtctactcgg tggcgaggcg   600
tggtcttcgt ggcataagga agactctatt catgtaggag tacgctgcat cgagatgctc   660
attgagtcaa ccggaatggt tagcttacac cgccaaaatg ctggcgtagt aggtcaagac   720
tctgagacta tcgaactcgc acctgaatac gctgaggcta tcgcaacccg tgcaggtgcg   780
ctggctggca tctctccgat gttccaacct tgcgtagttc ctcctaagcc gtggactggc   840
attactggtg gtggctattg ggctaacggt cgtcgtcctc tggcgctggt gcgtactcac   900
agtaagaaag cactgatgcg ctacgaagac gtttacatgc tgaggtgta caaagcgatt   960
aacattgcgc aaaacaccgc atggaaaatc aacaagaaag tcctagcggt cgccaacgta  1020
atcaccaagt ggaagcattg tccggtcgag acatccctg cgattgagcg tgaagaactc  1080
ccgatgaaac cggaagacat cgacatgaat cctgaggctc tcaccgcgtg gaaacgtgct  1140
gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg tcgtgttta cgctgtgtca atgttcaacc gcaaggtaa cgatatgacc  1320
aaaggactgc ttacgctggc gaaaggtaaa ccaatcggta aggaaggtta ctactggctg  1380
aaaatccacg gtgcaaactg tgcgggtgtc gataaggttc cgttccctga gcgcatcaag  1440
ttcattgagg aaaaccacga aacatcatg gcttgcgcta agtctccact ggagaacact  1500
tggtgggctg agcaagattc tccgttctgc ttccttgcgt tctgctttga gtacgctggg  1560
gtacagcacc acggcctgag ctataactgc tcccttccgc tggcgtttga cgggtcttgc  1620
tctggcatcc agcacttctc cgcgatgctc cgagatgagg taggtggtcg cgcggttaac  1680
ttgcttccta gtgaaaccgt tcaggacatc tacgggattc ttgctaagaa agtcaacgag  1740
attctacaag cagacgcaat caatgggacc gataacgaag tagttaccgt gaccgatgag  1800
aacactggtg aaatctctga gaaagtcaag ctgggcacta aggcactggc tggtcaatgg  1860
ctggcttacg tgttactcg cagtgtgact aagcgttcag tcatgacgct ggcttacggg  1920
tccaaagagt tcggcttccg tcaacaagtg ctggaagata ccattcagcc agctattgat  1980
```

```
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgttgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctatcgtgtg gcacacgag   2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 38
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: A702V, V795I variant (double mutant) of T7
      DNA-dependent RNA polymerase, amino acid sequence including
      N-terminal methionine; corresponding to #22 in Table 3

<400> SEQUENCE: 38

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
```

```
            195                 200                 205
Ser Ile His Val Gly Val Arg Cys Ile Glu Met Leu Ile Glu Ser Thr
210                     215                 220

Gly Met Val Ser Leu His Arg Gln Asn Ala Gly Val Val Gly Gln Asp
225                     230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
290                     295                 300

Leu Met Arg Tyr Glu Asp Val Tyr Met Pro Glu Val Tyr Lys Ala Ile
305                     310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
370                     375                 380

Tyr Arg Lys Asp Lys Ala Arg Lys Ser Arg Ile Ser Leu Glu Phe
385                     390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
450                     455                 460

Ala Asn Cys Ala Gly Val Asp Lys Val Pro Phe Pro Glu Arg Ile Lys
465                     470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
530                     535                 540

His Phe Ser Ala Met Leu Arg Asp Glu Val Gly Gly Arg Ala Val Asn
545                     550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
                610                 615                 620
```

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Val Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 39
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, A702V variant
      (double mutant) of T7 DNA-dependent RNA polymerase, including
      start codon encoding N-terminal methionine; corresponding to #23
      in Table 3

<400> SEQUENCE: 39
atgaacacga ttaacatcgc taagaacgac ttctctgaca tcgaactggc tgctatcccg      60
ttcaacactc tggctgacca ttacggtgag cgtttagctc gcaacagtt ggcccttgag     120 catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300

```
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtctgta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga cgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg tgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgttgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg gcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg attttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 40
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L, A702V variant (double mutant) of T7 DNA-dependent RNA polymerase, amino acid sequence including N-terminal methionine; corresponding to #23 in Table 3

<400> SEQUENCE: 40

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
```

```
                      325                 330                 335
        Val Ala Asn Val Ile Thr Lys Trp Lys His Cys Pro Val Glu Asp Ile
                      340                 345                 350
        Pro Ala Ile Glu Arg Glu Glu Leu Pro Met Lys Pro Glu Asp Ile Asp
                      355                 360                 365
        Met Asn Pro Glu Ala Leu Thr Ala Trp Lys Arg Ala Ala Ala Ala Val
                      370                 375                 380
        Tyr Arg Lys Asp Lys Ala Arg Lys Ser Arg Arg Ile Ser Leu Glu Phe
        385                 390                 395                 400
        Met Leu Glu Gln Ala Asn Lys Phe Ala Asn His Lys Ala Ile Trp Phe
                      405                 410                 415
        Pro Tyr Asn Met Asp Trp Arg Gly Arg Leu Tyr Ala Val Ser Met Phe
                      420                 425                 430
        Asn Pro Gln Gly Asn Asp Met Thr Lys Gly Leu Leu Thr Leu Ala Lys
                      435                 440                 445
        Gly Lys Pro Ile Gly Lys Glu Gly Tyr Tyr Trp Leu Lys Ile His Gly
                      450                 455                 460
        Ala Asn Cys Ala Gly Val Asp Lys Val Pro Phe Pro Glu Arg Ile Lys
        465                 470                 475                 480
        Phe Ile Glu Glu Asn His Glu Asn Ile Met Ala Cys Ala Lys Ser Pro
                      485                 490                 495
        Leu Glu Asn Thr Trp Trp Ala Glu Gln Asp Ser Pro Phe Cys Phe Leu
                      500                 505                 510
        Ala Phe Cys Phe Glu Tyr Ala Gly Val Gln His His Gly Leu Ser Tyr
                      515                 520                 525
        Asn Cys Ser Leu Pro Leu Ala Phe Asp Gly Ser Cys Ser Gly Ile Gln
                      530                 535                 540
        His Phe Ser Ala Met Leu Arg Asp Glu Val Gly Gly Arg Ala Val Asn
        545                 550                 555                 560
        Leu Leu Pro Ser Glu Thr Val Gln Asp Ile Tyr Gly Ile Val Ala Lys
                      565                 570                 575
        Lys Val Asn Glu Ile Leu Gln Ala Asp Ala Ile Asn Gly Thr Asp Asn
                      580                 585                 590
        Glu Val Val Thr Val Thr Asp Glu Asn Thr Gly Glu Ile Ser Glu Lys
                      595                 600                 605
        Val Lys Leu Gly Thr Lys Ala Leu Ala Gly Gln Trp Leu Ala Tyr Gly
                      610                 615                 620
        Val Thr Arg Ser Val Thr Lys Arg Ser Val Met Thr Leu Ala Tyr Gly
        625                 630                 635                 640
        Ser Lys Glu Phe Gly Phe Arg Gln Gln Val Leu Glu Asp Thr Ile Gln
                      645                 650                 655
        Pro Ala Ile Asp Ser Gly Lys Gly Leu Met Phe Thr Gln Pro Asn Gln
                      660                 665                 670
        Ala Ala Gly Tyr Met Ala Lys Leu Ile Trp Glu Ser Val Ser Val Thr
                      675                 680                 685
        Val Val Ala Ala Val Glu Ala Met Asn Trp Leu Lys Ser Val Ala Lys
                      690                 695                 700
        Leu Leu Ala Ala Glu Val Lys Asp Lys Lys Thr Gly Glu Ile Leu Arg
        705                 710                 715                 720
        Lys Arg Cys Ala Val His Trp Val Thr Pro Asp Gly Phe Pro Val Trp
                      725                 730                 735
        Gln Glu Tyr Lys Lys Pro Ile Gln Thr Arg Leu Asn Leu Met Phe Leu
                      740                 745                 750
```

```
Gly Gln Phe Arg Leu Gln Pro Thr Ile Asn Thr Asn Lys Asp Ser Glu
            755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880

Ala Phe Ala

<210> SEQ ID NO 41
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, V795I variant
      (double mutant) of T7 DNA-dependent RNA polymerase, including
      start codon encoding N-terminal methionine; corresponding to #24
      in Table 3

<400> SEQUENCE: 41
atgaacacga ttaacatcgc taagaacgac ttctctgaca tcgaactggc tgctatcccg     60
ttcaacactc tggctgacca ttacggtgag cgtttagctc gcaacagtt ggcccttgag    120 catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
```

-continued

```
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtctgta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 42
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L, V795I variant (double mutant) of T7 DNA-dependent RNA polymerase, amino acid sequence including N-terminal methionine; corresponding to #24 in Table 3

<400> SEQUENCE: 42

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30
```

```
Ala Arg Glu Gln Leu Ala Leu Glu His Glu Ser Tyr Glu Met Gly Glu
         35                  40                  45
Ala Arg Phe Arg Lys Met Phe Glu Arg Gln Leu Lys Ala Gly Glu Val
 50                  55                  60
Ala Asp Asn Ala Ala Lys Pro Leu Ile Thr Thr Leu Leu Pro Lys
 65                  70                  75                  80
Met Ile Ala Arg Ile Asn Asp Trp Phe Glu Val Lys Ala Lys Arg
                 85                  90                  95
Gly Lys Arg Pro Thr Ala Phe Gln Phe Leu Gln Glu Ile Lys Pro Glu
                100                 105                 110
Ala Val Ala Tyr Ile Thr Ile Lys Thr Thr Leu Ala Cys Leu Thr Ser
            115                 120                 125
Ala Asp Asn Thr Thr Val Gln Ala Val Ala Ser Ala Ile Gly Arg Ala
        130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
            180                 185                 190
Lys Gly Leu Leu Gly Gly Glu Ala Trp Ser Ser Trp His Lys Glu Asp
        195                 200                 205
Ser Ile His Val Gly Val Arg Cys Ile Glu Met Leu Ile Glu Ser Thr
    210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
            260                 265                 270
Val Pro Pro Lys Pro Trp Thr Gly Ile Thr Gly Gly Tyr Trp Ala
        275                 280                 285
Asn Gly Arg Arg Pro Leu Ala Leu Val Arg Thr His Ser Lys Lys Ala
    290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
            340                 345                 350
Pro Ala Ile Glu Arg Glu Glu Leu Pro Met Lys Pro Glu Asp Ile Asp
        355                 360                 365
Met Asn Pro Glu Ala Leu Thr Ala Trp Lys Arg Ala Ala Ala Val
370                 375                 380
Tyr Arg Lys Asp Lys Ala Arg Lys Ser Arg Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Leu Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
```

```
            450                 455                 460
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880
```

Ala Phe Ala

<210> SEQ ID NO 43
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, A702V, V795I
      variant (triple mutant) of T7 DNA-dependent RNA polymerase,
      including start codon encoding N-terminal methionine;
      corresponding to #25 in Table 3

<400> SEQUENCE: 43

```
atgaacacga ttaacatcgc taagaacgac ttctctgaca tcgaactggc tgctatcccg      60
ttcaacactc tggctgacca ttacggtgag cgtttagctc gcaacagtt ggcccttgag      120 catgagtctt acgagatggg tgaagcacgc ttccgcaaga tgtttgagcg tcaacttaaa     180
gctggtgagg ttgcggataa cgctgccgcc aagcctctca tcactaccct actccctaag    240
atgattgcac gcatcaacga ctggtttgag gaagtgaaag ctaagcgcgg caagcgcccg     300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgaccct tgaagctaag    480
cacttcaaga aaacgttga ggaacaactc aacaagcgcg tagggcacgt ctacaagaaa     540
gcatttatgc aagttgtcga ggctgacatg ctctctaagg gtctactcgg tgcgaggcg     600 tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc tgaggtgta caaagcgatt    960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg gtcgtctgta cgctgtgtca atgttcaacc cgcaaggtaa cgatatgacc    1320
aaaggactgc ttacgctggc gaaggtaaa ccaatcggta aggaaggtta ctactggctg    1380
aaaatccacg gtgcaaactg tgcgggtgtc gataaggttc cgttccctga gcgcatcaag    1440
ttcattgagg aaaccacga gaacatcatg gcttgcgcta gtctccact ggagaacact    1500 tggtgggctc agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
```

```
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 44
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L, A702V, V795I variant (triple mutant) of T7 DNA-dependent RNA polymerase, amino acid sequence including N-terminal methionine; corresponding to #25 in Table 3

<400> SEQUENCE: 44

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160
```

-continued

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn

```
                    580                 585                 590
Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Val Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 45
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, S633M, A702V,
      V795I variant (quadruple mutant) of T7 DNA-dependent RNA
      polymerase, including start codon encoding N-terminal methionine;
      corresponding to #26 in Table 3

<400> SEQUENCE: 45
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
```

-continued

```
catgagtctt acgagatggg tgaagcacgc ttccgcaaga tgtttgagcg tcaacttaaa      180
gctggtgagg ttgcggataa cgctgccgcc aagcctctca tcactaccct actccctaag      240
atgattgcac gcatcaacga ctggtttgag gaagtgaaag ctaagcgcgg caagcgcccg      300
acagccttcc agttcctgca agaaatcaag ccggaagccg tagcgtacat caccattaag      360
accactctgg cttgcctaac cagtgctgac aatacaaccg ttcaggctgt agcaagcgca      420
atcggtcggc ccattgagga cgaggctcgc ttcggtcgta tccgtgacct tgaagctaag      480
cacttcaaga aaacgttga ggaacaactc aacaagcgcg tagggcacgt ctacaagaaa       540
gcatttatgc aagttgtcga ggctgacatg ctctctaagg gtctactcgg tggcgaggcg      600
tggtcttcgt ggcataagga agactctatt catgtaggag tacgctgcat cgagatgctc      660
attgagtcaa ccggaatggt tagcttacac cgccaaaatg ctggcgtagt aggtcaagac      720
tctgagacta tcgaactcgc acctgaatac gctgaggcta tcgcaacccg tgcaggtgcg      780
ctggctggca tctctccgat gttccaacct tgcgtagttc ctcctaagcc gtggactggc      840
attactggtg gtggctattg ggctaacggt cgtcgtcctc tggcgctggt gcgtactcac      900
agtaagaaag cactgatgcg ctacgaagac gtttacatgc ctgaggtgta caaagcgatt      960
aacattgcgc aaaacaccgc atggaaaatc aacaagaaag tcctagcggt cgccaacgta     1020
atcaccaagt ggaagcattg tccggtcgag gacatccctg cgattgagcg tgaagaactc     1080
ccgatgaaac cggaagacat cgacatgaat cctgaggctc tcaccgcgtg gaaacgtgct     1140
gccgctgctg tgtaccgcaa ggacaaggct cgcaagtctc gccgtatcag ccttgagttc     1200
atgcttgagc aagccaataa gtttgctaac cataaggcca tctggttccc ttacaacatg     1260
gactggcgcg tcgtctgta cgctgtgtca atgttcaacc cgcaaggtaa cgatatgacc      1320
aaaggactgc ttacgctggc gaaaggtaaa ccaatcggta aggaaggtta ctactggctg     1380
aaaatccacg gtgcaaactg tgcgggtgtc gataaggttc cgttccctga gcgcatcaag     1440
ttcattgagg aaaaccacga aacatcatg gcttgcgcta agtctccact ggagaacact      1500
tggtgggctg agcaagattc tccgttctgc ttccttgcgt tctgctttga gtacgctggg     1560
gtacagcacc acggcctgag ctataactgc tcccttccgc tggcgtttga cgggtcttgc     1620
tctggcatcc agcacttctc cgcgatgctc cgagatgagg taggtggtcg cgcggttaac     1680
ttgcttccta gtgaaaccgt tcaggacatc tacgggattg ttgctaagaa agtcaacgag     1740
attctacaag cagacgcaat caatgggacc gataacgaag tagttaccgt gaccgatgag     1800
aacactggtg aaatctctga aaagtcaag ctgggcacta aggcactggc tggtcaatgg      1860
ctggcttacg gtgttactcg cagtgtgact aagcgtatgg tcatgacgct ggcttacggg     1920
tccaaagagt tcggcttccg tcaacaagtg ctggaagata ccattcagcc agctattgat     1980
tccggcaagg gtctgatgtt cactcagccg aatcaggctg ctggatacat ggctaagctg     2040
atttgggaat ctgtgagcgt gacggtggta gctgcggttg aagcaatgaa ctggcttaag     2100
tctgttgcta agctgctggc tgctgaggtc aaagataaga agactggaga gattcttcgc     2160
aagcgttgcg ctgtgcattg ggtaactcct gatggtttcc ctgtgtggca ggaatacaag     2220
aagcctattc agacgcgctt gaacctgatg ttcctcggtc agttccgctt acagcctacc     2280
attaacacca acaaagatag cgagattgat gcacacaaac aggagtctgg tatcgctcct     2340
aactttgtac acagccaaga cggtagccac cttcgtaaga ctatcgtgtg gcacacgag      2400 aagtacggaa tcgaatcttt tgcactgatt cacgactcct tcggtaccat tccggctgac     2460
```

```
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                     2655
```

<210> SEQ ID NO 46
<211> LENGTH: 883
<212> TYPE: PRT
<213> ORGANISM: Artificial Sequence
<220> FEATURE:
<223> OTHER INFORMATION: Description of Artificial Sequence: Synthetic
      variant polypeptide
<220> FEATURE:
<221> NAME/KEY: misc_feature
<222> LOCATION: (1)..(883)
<223> OTHER INFORMATION: V426L, S633M, A702V, V795I variant (quadruple
      mutant) of T7 DNA-dependent RNA polymerase, amino acid sequence
      including N-terminal methionine; corresponding to #26 in Table 3

<400> SEQUENCE: 46

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285
```

-continued

```
Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Met Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
    690                 695                 700

Leu Leu Ala Ala Glu Val Lys Asp Lys Lys Thr Gly Glu Ile Leu Arg
```

| | | | | |
|---|---|---|---|---|
| 705 | | 710 | 715 | 720 |

Lys Arg Cys Ala Val His Trp Val Thr Pro Asp Gly Phe Pro Val Trp
                   725                       730                   735

Gln Glu Tyr Lys Lys Pro Ile Gln Thr Arg Leu Asn Leu Met Phe Leu
              740                     745                   750

Gly Gln Phe Arg Leu Gln Pro Thr Ile Asn Thr Asn Lys Asp Ser Glu
         755                   760                   765

Ile Asp Ala His Lys Gln Glu Ser Gly Ile Ala Pro Asn Phe Val His
770                   775                     780

Ser Gln Asp Gly Ser His Leu Arg Lys Thr Ile Val Trp Ala His Glu
785                   790                   795                800

Lys Tyr Gly Ile Glu Ser Phe Ala Leu Ile His Asp Ser Phe Gly Thr
                 805                   810                   815

Ile Pro Ala Asp Ala Ala Asn Leu Phe Lys Ala Val Arg Glu Thr Met
            820                     825                   830

Val Asp Thr Tyr Glu Ser Cys Asp Val Leu Ala Asp Phe Tyr Asp Gln
         835                   840                   845

Phe Ala Asp Gln Leu His Glu Ser Gln Leu Asp Lys Met Pro Ala Leu
850                   855                   860

Pro Ala Lys Gly Asn Leu Asn Leu Arg Asp Ile Leu Glu Ser Asp Phe
865                   870                   875                880

Ala Phe Ala

<210> SEQ ID NO 47
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, V650L, A702V,
      V795I variant (quadruple mutant) of T7 DNA-dependent RNA
      polymerase, including start codon encoding N-terminal methionine;
      corresponding to #27 in Table 3

<400> SEQUENCE: 47

| | |
|---|---|
| atgaacacga ttaacatcgc taagaacgac ttctctgaca tcgaactggc tgctatcccg | 60 |
| ttcaacactc tggctgacca ttacggtgag cgtttagctc gcgaacagtt ggcccttgag | 120 |
| catgagtctt acgagatggg tgaagcacgc ttccgcaaga tgtttgagcg tcaacttaaa | 180 |
| gctggtgagg ttgcggataa cgctgccgcc aagcctctca tcactaccct actccctaag | 240 |
| atgattgcac gcatcaacga ctggtttgag gaagtgaaag ctaagcgcgg caagcgcccg | 300 |
| acagccttcc agttcctgca agaaatcaag ccggaagccg tagcgtacat caccattaag | 360 |
| accactctgg cttgcctaac cagtgctgac aatacaaccg ttcaggctgt agcaagcgca | 420 |
| atcggtcggc ccattgagga cgaggctcgc ttcggtcgta ccgtgaccct gaagctaag | 480 |
| cacttcaaga aaacgttga ggaacaactc aacaagcgcg tagggcacgt ctacaagaaa | 540 |
| gcatttatgc aagttgtcga ggctgacatg ctctctaagg gtctactcgg tggcgaggcg | 600 |
| tggtcttcgt ggcataagga agactctatt catgtaggag tacgctgcat cgagatgctc | 660 |
| attgagtcaa ccggaatggt tagcttacac cgccaaaatg ctggcgtagt aggtcaagac | 720 |
| tctgagacta cgaactcgc acctgaatac gctgaggcta cgcaacccg tgcaggtgcg | 780 |
| ctggctggca tctctccgat gttccaacct tgcgtagttc ctcctaagcc gtggactggc | 840 |

```
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg tcgtctgta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga cgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga aaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaactg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgttgcta agctgctggc tgctgaggtc aaagataaga gactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctatcgtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aataa                                                    2655
```

<210> SEQ ID NO 48
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L, V650L, A702V, V795I variant (quadruple mutant) of T7 DNA-dependent RNA polymerase, amino acid sequence including N-terminal methionine; corresponding to #27 in Table 3

<400> SEQUENCE: 48

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65              70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415
```

```
Pro Tyr Asn Met Asp Trp Arg Gly Arg Leu Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Leu Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
```

835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 49
<211> LENGTH: 2655
<212> TYPE: DNA
<213> ORGANISM: Artificial Sequence
<220> FEATURE:
<223> OTHER INFORMATION: Description of Artificial Sequence: Synthetic
      coding polynucleotide
<220> FEATURE:
<221> NAME/KEY: misc_feature
<222> LOCATION: (1)..(2655)
<223> OTHER INFORMATION: DNA sequence encoding the V426L, S633M, V650L,
      A702V, V795I variant (quintuple mutant) of T7 DNA-dependent RNA
      polymerase, including start codon encoding N-terminal methionine;
      corresponding to #28 in Table 3

<400> SEQUENCE: 49
atgaacacga ttaacatcgc taagaacgac ttctctgaca tcgaactggc tgctatcccg        60
ttcaacactc tggctgacca ttacggtgag cgtttagctc gcgaacagtt ggcccttgag       120
catgagtctt acgagatggg tgaagcacgc ttccgcaaga tgtttgagcg tcaacttaaa       180
gctggtgagg ttgcggataa cgctgccgcc aagcctctca tcactaccct actccctaag       240
atgattgcac gcatcaacga ctggtttgag gaagtgaaag ctaagcgcgg caagcgcccg       300
acagccttcc agttcctgca agaaatcaag ccggaagccg tagcgtacat caccattaag       360
accactctgg cttgcctaac cagtgctgac aatacaaccg ttcaggctgt agcaagcgca       420
atcggtcggg ccattgagga cgaggctcgc ttcggtcgta tccgtgacct tgaagctaag       480
cacttcaaga aaaacgttga ggaacaactc aacaagcgcg tagggcacgt ctacaagaaa       540
gcatttatgc aagttgtcga ggctgacatg ctctctaagg tctactcgg tggcgaggcg        600 tggtcttcgt ggcataagga agactctatt catgtaggag tacgctgcat cgagatgctc       660
attgagtcaa ccggaatggt tagcttacac cgccaaaatg ctggcgtagt aggtcaagac       720
tctgagacta tcgaactcgc acctgaatac gctgaggcta tcgcaacccg tgcaggtgcg       780
ctggctggca tctctccgat gttccaacct tgcgtagttc ctcctaagcc gtggactggc       840
attactggtg gtggctattg gctaacggt cgtcgtcctc tggcgctggt gcgtactcac       900
agtaagaaag cactgatgcg ctacgaagac gtttacatgc ctgaggtgta caaagcgatt       960
aacattgcgc aaaacaccgc atggaaaatc aacaagaaag tcctagcggt cgccaacgta      1020
atcaccaagt ggaagcattg tccggtcgag acatccctg cgattgagcg tgaagaactc       1080
ccgatgaaac cggaagacat cgacatgaat cctgaggctc tcaccgcgtg aaacgtgct       1140 gccgctgctg tgtaccgcaa ggacaaggct cgcaagtctc gccgtatcag ccttgagttc       1200
atgcttgagc aagccaataa gtttgctaac cataaggcca tctggttccc ttacaacatg      1260
gactggcgcg tcgtctgta cgctgtgtca atgttcaacc gcaaggtaa cgatatgacc       1320 aaaggactgc ttacgctggc gaaagtaaa ccaatcggta aggaaggtta ctactggctg      1380
aaaatccacg gtgcaaactg tgcgggtgtc gataaggttc cgttccctga gcgcatcaag      1440
ttcattgagg aaaccacga gaacatcatg gcttgcgcta gtctccact ggagaacact      1500 tggtgggctg agcaagattc tccgttctgc ttccttgcgt tctgctttga gtacgctggg      1560

-continued

```
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgtatgg tcatgacgct ggcttacggg    1920
tccaaagagt tcggcttccg tcaacaactg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgttgcta agctgctggc tgctgaggtc aaagataaga agactggaga gattcttcgc    2160
aagcgttgcg ctgtgcattg gtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctatcgtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655
```

<210> SEQ ID NO 50
<211> LENGTH: 883
<212> TYPE: PRT
<213> ORGANISM: Artificial Sequence
<220> FEATURE:
<223> OTHER INFORMATION: Description of Artificial Sequence: Synthetic variant polypeptide
<220> FEATURE:
<221> NAME/KEY: misc_feature
<222> LOCATION: (1)..(883)
<223> OTHER INFORMATION: V426L, S633M, V650L, A702V, V795I variant (quintuple mutant) of T7 DNA-dependent RNA polymerase, amino acid sequence including N-terminal methionine; corresponding to #28 in Table 3

<400> SEQUENCE: 50

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
```

```
            115                 120                 125
Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Leu Tyr Ala Val Ser Met Phe
                420                 425                 430

Asn Pro Gln Gly Asn Asp Met Thr Lys Gly Leu Leu Thr Leu Ala Lys
    435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
                530                 535                 540
```

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Met Val Met Thr Leu Ala Tyr Gly
625                 630                 635                 640

Ser Lys Glu Phe Gly Phe Arg Gln Gln Leu Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Val Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Ile Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA encoding N-terminal Histidine (His6) tag
      with linker sequence, fused to the first two N-terminal amino
      acids of T7 (Met and Asn)
<220> FEATURE:

```
<221> NAME/KEY: misc_feature
<222> LOCATION: (28)..(33)
<223> OTHER INFORMATION: codons encoding the first two T7 amino acids
      Met and Asn
<220> FEATURE:
<221> NAME/KEY: misc_feature
<222> LOCATION: (31)..(33)
<223> OTHER INFORMATION: codon corresponding to positions 4 to 6 in each
      of SEQ ID NOs: 1, 3, 5, 7, 9, 11, 13, 15, 17, 19, 21, 23, 25, 27,
      29, 31, 33, 35, 37, 39, 41, 43, 45, 47, 49

<400> SEQUENCE: 51
atgcatcacc atcatcacca cggatccatg aac                                    33

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino acid sequence of N-terminal Histidine
      (His6) tag with linker sequence, fused to the first two N-terminal
      amino acids of T7 (Met and Asn)
<220> FEATURE:
<221> NAME/KEY: misc_feature
<222> LOCATION: (2)..(7)
<223> OTHER INFORMATION: Histidine-tag (His6)
<220> FEATURE:
<221> NAME/KEY: misc_feature
<222> LOCATION: (8)..(9)
<223> OTHER INFORMATION: Linker sequence
<220> FEATURE:
<221> NAME/KEY: misc_feature
<222> LOCATION: (11)..(11)
<223> OTHER INFORMATION: Amino acid Asn corresponding to Asn on position
      2 of each of SEQ ID NOs: 2, 4, 6, 8, 10, 12, 14, 16, 18, 20, 22,
      24, 26, 28, 30, 32, 34, 36, 38, 40, 42, 44, 46, 48, 50

<400> SEQUENCE: 52

Met His His His His His His Gly Ser Met Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(7)
<223> OTHER INFORMATION: This region may encompass 3 to 7 "His" residues
<220> FEATURE:
<223> OTHER INFORMATION: see specification as filed for detailed
      description of substitutions and preferred embodiments

<400> SEQUENCE: 53

His His His His His His His
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 54

His His His His His His
1               5
```

T7 RNA POLYMERASE VARIANTS WITH ENHANCED THERMOSTABILITY

RELATED APPLICATIONS

This application claims priority to European application EP 10004059.1 filed Apr. 16, 2010.

SEQUENCE LISTING

The instant application contains a Sequence Listing which has been submitted in ASCII format via EFS-Web and is hereby incorporated by reference in its entirety. Said ASCII copy, created on Mar. 17, 2011, is named 26576US.txt, and is 297,574 bytes in size.

FIELD OF THE INVENTION

The invention pertains to the field of biochemistry, particularly to the field of enzyme engineering.

The present invention provides improved variants of T7 RNA polymerase by introducing novel mutations which lead to improved thermostability of the enzyme. According to the invention, amino acid substitutions at the positions Val426, Ser633, Val650, Thr654, Ala702, Val795, and combinations thereof are advantageous.

BACKGROUND OF THE INVENTION

T7 RNA polymerase (E.C. 2.7.7.6.; herein also referred to as "T7 polymerase" or "T7") is a monomeric bacteriophage encoded DNA directed RNA polymerase which catalyzes the formation of RNA in the 5'→3' direction. In the process of initiation of transcription T7 recognizes a specific promoter sequence, the T7 promoter. T7 consists of 883 amino acids and has a molecular weight of 99 kDa. On the level of amino acid sequence T7 is highly homologous to T3 RNA polymerase and, to a lesser extent, SP6 RNA polymerase. The three-dimensional structure of T7 is very similar to other polymerases with different template and substrate specificities, despite low sequence similarity. T7 consists of different domains, the N-terminal domain, the "thumb", the "palm" and the "fingers" (Sousa, R., and Mukherjee, S., Prog. Nucl. Acid Res. Mol. Biol. 73 (2003) 1-41).

Detailed studies of the transcription reaction showed that the enzyme acts like a molecular machine showing well concerted movements of flexible parts of the enzyme (Steitz, T. A., EMBO J. 25 (2006) 3458-3468; Steitz, T. A., Curr. Opin. Struct. Biol. 14 (2004) 4-9; Yin, Y. W., and Steitz, T. A., Cell 116 (2004) 393-404).

Several structures of T7 in complex with promoter DNA were solved and are available in the Protein Data Bank (pdb). The structure of the initiation complex of T7 RNA polymerase was solved at high resolution (Cheetham, G. M. T., et al., Nature 399 (1999) 80-83; Cheetham, G. M. T., and Steitz, T. A., Science 286 (1999) 2305-2309). The structure of the elongation complex solved at 2.9 Å resolution showed the rearrangement of the N-terminal region (Tahirov, T. H., et al., Nature 420 (2002) 43-50). The structural studies showed that the conformation of the N-terminal domain changes between the initiation and elongation phases. Recently, the structure of transcribing T7 in transition from initiation to elongation phase was described (Durniak, K. J., et al., Science 322 (2008) 553-557).

The cloning and the expression of the gene encoding T7 has been described (Studier et al., U.S. Pat. No. 4,952,496). T7 has been studied intensively by mutagenesis to explore the conformational changes during transcription (Ma, K., et. al., Proc. Nat. Acad. Sci. 102 (2005) 17612-17617), to facilitate promoter clearance (Guillerez, J., et al., Proc. Natl. Acad. Sci. 102 (2005) 5958-5963) or to study the abortive cycling phenomenon (He, B., et al., J. Mol. Biol. 265 (1997) 275-288). Bonner, G., et al., J. Biol. Chem. 269 (1994) 25120-25128 described a set of active site mutants with altered elongation rates.

Due to the promoter specificity and high RNA polymerase enzymatic activity, T7 is useful for a variety of applications in molecular biology. In the field of recombinant protein expression T7 is used for the high-level expression of recombinant genes in *E. coli* (Studier, F. W., and Moffat, B. A., J. Mol. Biol. 189 (1986) 113-130). The synthesis of defined oligoribonucleotides was described by Milligan, J. F., et al., Nucl. Aids Res. 15 (1987) 8783-8798.

In addition, T7 is used in nucleic acid amplification methods for diagnostic purposes. A first example for such use is a technique known as "Nucleic Acid Sequence Based Amplification" (NASBA). This process comprises the steps of (a) adding a RNA template to a reaction mixture, wherein a first primer anneals to a complementary site at the 3' end of the template; (b) reverse transcribing a DNA strand complementary to the RNA template, wherein a RNA/DNA heteroduplex is formed; (c) degrading the RNA strand of the heteroduplex by way of RNaseH activity; (d) annealing a second primer to the 5' end of the DNA strand; (e) repeatedly synthesizing a complementary RNA strand with T7 RNA polymerase, wherein the synthesized RNA strand can serve again as a template in step (a). The NASBA technique has been used to develop rapid diagnostic tests for several pathogenic viruses, particularly those with single-stranded RNA genomes.

A further example for a diagnostic isothermal amplification method is "Transcription mediated amplification" (TMA) known to be one of the most sensitive detection assays for hepatitis C virus RNA in patient serum. For amplification of target RNA, two enzymes are used which are reverse transcriptase (RT) and T7 RNA polymerase. Complementary DNA (cDNA) of sample RNA is generated by RT with RNAse H activity and a primer containing a T7-promoter at the 5'-end. The RNA resulting of the RNA-DNA duplex is degraded by RNAse H activity of the RT. Another primer then binds to the cDNA already containing the T7-promoter sequence from the first primer and a double-stranded DNA is synthesized by the DNA polymerase activity of the RT. The T7 RNA polymerase recognizes the T7-promoter sequence within the double-stranded DNA molecule and synthesizes numerous RNA antisense transcripts. Each of the newly produced RNA amplicons re-enters the TMA process and serves as a template for a new round of RT to double-stranded DNA including the T7-promoter and transcription of antisense amplicons. The circulation of antisense transcripts into the amplification process results in exponential amplification of target RNA.

For NASBA, TMA and related methods as well as for other applications it would be advantageous if the reaction temperature could be elevated to improve the reaction kinetics. E.g., higher reaction temperatures of isothermal amplification could allow the amplification of RNA having secondary structures. It has also been shown with the polymerase chain reaction (PCR) technology that high annealing temperatures allow the specific hybridization of a primer to its target resulting in a highly specific amplification. With the same advantage, more thermostable enzymes could in principle also be applied isothermal amplifications.

Therefore, there is a need of a T7 RNA polymerase with improved stability and activity at higher reaction temperatures.

The stability of T7 RNA polymerase has been studied extensively. Thermal and urea-induced unfolding of was studied by Protasevich et al. using calorimetry, circular dichronism and fluorescence (Protasevich, I. I., et al., FEBS Lett 349 (1994) 429-432). Under the conditions used the enzyme unfolded at 48.3° C. Thermal unfolding was also studied by Griko et al. using calorimetric methods (Griko, Y., et al., Prot. Sci. (2001) 845-853). A smaller 22 kDa N-terminal part of the enzyme was shown to increase the thermostability of the C-terminal 77 kDa domain.

By introducing point mutations in the sequence of the wild-type enzyme T7 variants were generated in which the stability of T7 RNA polymerase was enhanced. The U.S. Pat. No. 6,524,828 and EP 1 261 696 describe four distinct amino acid exchanges in the T7 RNA polymerase polypeptide (Ser430Pro, Ser633Pro, Phe849Ile and Phe880Tyr) which stabilize the enzyme. Combinations of two or more of these mutations in a modified T7 polypeptide result in even more stable enzyme variants.

The aim of the present invention was to extend the collection of stabilizing mutations by creating novel mutations in T7 RNA polymerase which lead to improved stability. It is further desired to combine several of these mutations in a single T7 variant (double-, triple-, quadruple-, multiple-mutant), provided the combined mutations lead to an even increased stability, that is to say thermostability. According to the invention, new mutations are found giving rise to T7 variants which exhibit high stability in thermal unfolding assays.

SUMMARY OF THE INVENTION

A first aspect of the invention is a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, wherein the variant comprises a polypeptide of the wild-type reference in which at least one amino acid and up to four amino acids at different positions is/are substituted, wherein a different amino acid substitutes for an amino acid selected from the group consisting of Val426, Ser633, Val650, Thr654, Ala702, and Val795, numbered from the N-terminus of the wild-type reference, and wherein the different amino acid is selected from the group consisting of Leu, Ile and Phe when the different amino acid substitutes for Val426 (Val426Leu, Val426Ile, Val426Phe), Val and Met when the different amino acid substitutes for Ser633 (Ser633Val, Ser633Met), Leu when the different amino acid substitutes for Val650 (Val650Leu), Leu when the different amino acid substitutes for Thr654 (Thr654Leu), Val when the different amino acid substitutes for Ala702 (Ala702Val), Ile when the different amino acid substitutes for Val795 (Val795Ile).

In a first embodiment, a different amino acid substitutes for an amino acid selected from the group consisting of Val426, Val650, Ala702, and Val795. In a preferred embodiment, four amino acids at different positions are substituted, and the different amino acids are Val426Leu, Val650Leu, Ala702Val, and Val795Ile. In yet a further preferred embodiment, a different amino acid substitutes for an amino acid selected from the group consisting of Val426, Ala702, and Val795, and wherein up to three amino acids at different positions is/are substituted. In yet a further preferred embodiment, two or three amino acids at different positions are substituted, and the different amino acids are selected from the group consisting of Val426Leu, Ala702Val, and Val795Ile. In yet a further preferred embodiment, three amino acids at different positions are substituted and the different amino acids are Val426Leu, Ala702Val, and Val795Ile.

A second aspect of the invention is a method to produce a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said method comprising the steps of (a) selecting an amino acid from the group consisting of Val426, Ser633, Val650, Thr654, Ala702, and Val795, numbered from the N-terminus of the wild-type reference; (b) substituting a selected amino acid with a different amino acid to form a T7 variant, wherein the different amino acid is selected from the group consisting of Leu, Ile and Phe when the different amino acid substitutes for Val426 (Val426Leu, Val426Ile, Val426Phe), Val and Met when the different amino acid substitutes for Ser633 (Ser633Val, Ser633Met), Leu when the different amino acid substitutes for Val650 (Val650Leu), Leu when the different amino acid substitutes for Thr654 (Thr654Leu), Val when the different amino acid substitutes for Ala702 (Ala702Val), Ile when the different amino acid substitutes for Val795 (Val795Ile), wherein of the wild-type reference at least one amino acid and up to four amino acids at different positions is/are substituted; (c) expressing a nucleic acid molecule encoding the T7 variant with the substituted amino acids of step (b) in a transformed host organism, and isolating the expressed T7 variant from the host organism; thereby producing the T7 variant.

A third aspect of the invention is a method to produce a nucleic acid molecule encoding a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said method comprising the steps of (a) reverse transcribing an amino acid sequence of a polypeptide according to the invention or an amino acid sequence of a polypeptide obtainable by the method according to the invention, thereby obtaining a nucleic acid sequence; followed by (b) synthesizing a nucleic acid molecule with the nucleic acid sequence obtained after performing step (a); thereby producing the nucleic acid molecule encoding the T7 variant.

A preferred embodiment of the invention is a nucleic acid molecule with a sequence encoding a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said nucleic acid being obtainable by the method of the invention. Yet, a further preferred embodiment of the invention is a nucleic acid molecule, wherein said nucleic acid is selected from the group consisting of SEQ ID NO: 9, SEQ ID NO: 11, SEQ ID NO: 19, SEQ ID NO: 21, SEQ ID NO: 23, SEQ ID NO: 25, SEQ ID NO: 29, SEQ ID NO: 37, SEQ ID NO: 39, SEQ ID NO: 41, SEQ ID NO: 43, and SEQ ID NO: 47.

A fourth aspect of the invention is an expression vector comprising a nucleic acid molecule according to the invention, wherein said nucleic acid molecule is functionally linked to one or more sequences capable of controlling transcription and/or translation.

A fifth aspect of the invention is a host organism capable of recombinant expression of a polypeptide, wherein said host organism is transformed with an expression vector according to the invention.

A sixth aspect of the invention is a method to synthesize a RNA molecule, comprising the steps of (a) providing a template DNA molecule comprising a T7 promoter, said T7 promoter being functionally linked to a target nucleotide sequence to be transcribed; (b) contacting the template DNA of step (a) with a variant polypeptide of T7 RNA polymerase (T7 variant) according to the invention or a T7 variant obtainable by the method of the invention; followed by (c) incubating the template DNA and the T7 variant in the presence of ribonucleoside triphosphates; thereby synthesizing the RNA molecule.

A seventh aspect of the invention is a composition comprising a template DNA molecule with a T7 promoter functionally coupled to a target nucleotide sequence to be transcribed, ribonucleoside triphosphates, and a variant polypeptide of T7 RNA polymerase (T7 variant) according to the invention or a T7 variant obtainable by the method according to the invention.

An eighth aspect of the invention is a kit comprising, in separate containers, a variant polypeptide of T7 RNA polymerase (T7 variant) according to the invention or a T7 variant obtainable by the method according to the invention and a buffer with one or more ribonucleoside triphosphates.

DETAILED DESCRIPTION OF THE INVENTION

The present invention aims at providing the skilled person with novel variants of T7 polymerase which are characterized by (i) a DNA-dependent RNA polymerase enzymatic activity, (ii) an enhanced thermostability compared to the wild-type T7 RNA polymerase polypeptide (wild-type reference), and (iii) a different composition of amino acids compared to the wild-type reference. Such a "variant" is an allelic form of the wild-type T7 protein, wherein said variant is generated by way of amino acid substitution.

Certain terms are used with particular meaning or are defined for the first time in this description of the present invention. For the purposes of the invention, the terms used are defined by their art-accepted definitions, when such exist, except that when those definitions conflict or partially conflict with the definitions set forth below. In the event of a conflict in definition, the meaning of a term is first defined by any of the definitions set forth in this document.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a compound" means one compound or more than one compound.

If not stated otherwise, it is understood that the term "about" in combination with a numerical value n ("about n") indicates a value x in the interval given by the numerical value ±5% of the value, i.e., $n-0.05*n \leq x \leq n+0.05*n$. In case the term "about" in combination with a numerical value n describes a preferred embodiment of the invention, the value of n is most preferred, if not indicated otherwise.

A nucleotide sequence "encodes" a peptide or polypeptide when at least a portion of the nucleic acid, or its complement, can be directly translated to provide the amino acid sequence of the peptide or protein, or when the isolated nucleic acid can be used, alone or as part of an expression vector, to express the peptide or protein in vitro, in a prokaryotic host cell, or in a eukaryotic host cell.

Where a nucleotide sequence is single-stranded, it is to be understood that the complementary sequence of that nucleotide sequence is also included within the scope of the present invention.

The coding portion of a nucleotide sequence encoding a peptide or a polypeptide begins with a start codon encoding Methionine which thus becomes the N-terminal amino acid of the primary translation product. As part of post-translational processes, the N-terminal Methionine is frequently cleaved off, e.g., by a Methionine aminopeptidase which is a ubiquitous enzyme. In such a case, the primary translation product may give rise to a mixture comprising members without N-terminal Methionine and members retaining this amino acid as N-terminus. It is also possible that the form of the enzyme without N-terminal Methionine is the only one which can be isolated. However, the amino acid sequences of the wild-type T7 polymerase and the T7 variants according to the invention are described in the sequence listing including N-terminal Methionine. But the present invention also encompasses the said T7 variants which do not include N-terminal Methionine.

For purposes of shorthand designation of T7 polymerase variants described herein, it is noted that for each mutation a number refers to the amino acid residue/position along the reference amino acid sequence of the wild-type T7 polymerase protein given in SEQ ID NO: 2. Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, H is H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine. An amino acid at a particular position in an amino acid sequence is given by its three-letter abbreviation and a number. Accordingly, any of "Leu705" and "L705" denote the leucine residue at amino acid position 705 in SEQ ID NO: 2. In any T7 mutant and/or T7 variant disclosed herein, a substitution by a different amino acid is given as the three-letter abbreviation added after the number indicating the position. E.g., "Leu705Ile" (=[Leu705Ile]) or "L705I" (=[L705I]) denote the substitution of Leu at position 705 in SEQ ID NO: 2 by Ile (see #16 of Table 3). A Leu705Ile (=L705I) substitution results in an amino acid sequence as given in SEQ ID NO: 28, encoded by the nucleotide sequence of SEQ ID NO: 27. Preferred amino acid substitutions are disclosed in Table 1 further below (see Example 1). Particularly preferred variants according to the invention are characterized by a plurality (preferred 2 to 4) of amino acid substitutions. Examples therefor can be found in Table 4, for example—but not limited to—#24 [Val426Leu, Val795Ile] or #25 [Val426Leu, Ala702Val, Val795Ile].

The term "polypeptide" or "protein" denotes a polymer composed of a plurality of amino acid monomers joined by peptide bonds. Preferably, the polymer comprises 50 or more monomers. A preferred polypeptide or protein according to the invention is a T7 variant. A "peptide bond" is a covalent bond between a first amino acid and a second amino acid in which the α-amino group of the first amino acid is bonded to the α-carboxyl group of the second amino acid.

The T7 variants of the invention also comprise fusion proteins with an affinity tag such as, but not limited to, a Histidine tag (His-tag). Well known to the skilled artisan, a His-tag is an amino acid sequence containing several, preferably 3 to 7, more preferred 6 consecutive Histidines (SEQ ID NO: 53). In a His-tag sequence the Histidines represent the essential portion. But facultatively there are few additional amino acids comprised in the His-tag. For example, a N-terminal T7 sequence including a His-tag can comprise the sequence N-Met His His His His His His Gly Ser-(residues 1-9 of SEQ ID NO: 52). To this end see SEQ ID NO: 52 comprising the foregoing amino acid sequence. In the present exemplary His-tag the amino acids Gly and Ser form a linker to the N-terminus of the T7 variant. The linker amino acids are part of the His-tag and typically arise as a cloning artifact of the nucleotide sequence encoding the His-tag (e.g., SEQ ID NO: 51). Preferably, the linker sequence in the His-tag comprises 1 to 5 amino acids.

According to the invention, the N-terminal Methionine of a T7 variant can be replaced by a His-tag. Alternatively, the N-terminal sequence of the T7 variant according to the invention can be extended by the His-tag. In such a case, the N-terminus of the primary translation product of the T7 variant comprises a N-terminal Methionine followed by the His-tag, followed by the Methionine encoded by the start codon of the original T7 encoding nucleotide sequence.

Purification of a His-tagged T7 wild-type or variant polypeptide is efficiently performed by immobilized metal affinity chromatography. This method is a widely employed method to purify recombinant proteins containing a short affinity-tag consisting of Histidine residues (His-tag). Immobilized metal-affinity chromatography (described by Porath, J., et al., Nature 258 (1975) 598-599) is based on the interaction between a transition metal ion ($Co^{2+}$, $Ni^{2+}$, $Cu^{2+}$, $Zn^{2+}$) immobilized on a particulate metal chelating affinity matrix and specific amino acid side chains. Histidine is the amino acid that exhibits the strongest interaction with immobilized metal ion matrices, as electron donor groups on the Histidine imidazole ring readily form coordination bonds with the immobilized transition metal.

A "vector" is defined as a DNA which can comprise, i.e., carry, and maintain a DNA fragment according to the invention, including, for example, phages and plasmids. These terms are understood by those of skill in the art of genetic engineering. The term "expression cassette" denotes a nucleotide sequence encoding a pre-protein, operably linked to a promoter and a terminator. As for vectors containing an expression cassette, the terms "vector" and "expression vector" are used as synonyms.

The term "oligonucleotide" is used for a nucleic acid molecule, DNA (or RNA), with less than 100 nucleotides in length. Preferably, an oligonucleotide is about 75, about 50 or less nucleotides in length "Transformation" means introducing DNA into an organism, i.e., a host organism, so that the DNA is replicable, either as an extrachromosomal element or by chromosomal integration.

The term "expression" and the verb "to express" denote transcription of DNA sequences and/or the translation of the transcribed mRNA in a host organism resulting in a pre-protein, i.e., not including post-translational processes.

A "promoter" is a regulatory nucleotide sequence that stimulates transcription. These terms are understood by those of skill in the art of genetic engineering. Like a promoter, a "promoter element" stimulates transcription but constitutes a sub-fragment of a larger promoter sequence.

The term "operably linked" refers to the association of two or more nucleic acid fragments on a single vector so that the function of one is affected by the other. For example, a promoter is operably linked with a coding sequence, i.e., a nucleotide sequence encoding a protein or a pre-protein, when it is capable of affecting the expression of that coding sequence, i.e., that the coding sequence is under the transcriptional control of the promoter.

According to the invention, a first embodiment is a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, wherein the variant comprises a polypeptide of the wild-type reference in which at least one amino acid and up to four amino acids at different positions is/are substituted, wherein a different amino acid substitutes for an amino acid selected from the group consisting of Val426, Ser633, Val650, Thr654, Ala702, and Val795, numbered from the N-terminus of the wild-type reference, and wherein the different amino acid is selected from the group consisting of Leu, Ile and Phe when the different amino acid substitutes for Val426 (Val426Leu, Val426Ile, Val426Phe), Val and Met when the different amino acid substitutes for Ser633 (Ser633Val, Ser633Met), Leu when the different amino acid substitutes for Val650 (Val650Leu), Leu when the different amino acid substitutes for Thr654 (Thr654Leu), Val when the different amino acid substitutes for Ala702 (Ala702Val), Ile when the different amino acid substitutes for Val795 (Val795Ile).

The experimental work underlying the above selections basically followed a rational approach to introduce at selected positions predetermined amino acid substitutions in the T7 polypeptide. Among a large number of mutations tested, several unexpectedly inhibited T7 polymerase activity, others—against the prediction—did not noticeably enhance thermostability; only a few mutations in fact showed the desired effects.

Since the development of site-directed mutagenesis protocols, modification of enzyme-encoding nucleotide sequences has become a powerful method in the field of protein engineering (Winter, G., et al., Nature 299 (1982) 756-758). The knowledge of the structure of an enzyme—combined with detailed biochemical data concerning the principles underlying its function and stability—offers the opportunity to rationally design enzymes with improved properties. Examples for improvements are, e.g., enhanced specificity, altered substrate spectrum, and thermostability. The latter kind of improvements is pursued in the present case.

Fersht & Serrano discussed general principles of protein stability derived from protein engineering experiments (Fersht, A. R., and Serrano, L., Curr. Opin. Struct. Biol. 3 (1993) 75-83). The specific interactions between amino acids in a protein and the effect on stability were described. With regards to the stabilization of a protein an improvement was exemplified by "filling" hydrophobic cavities in the inner core of a protein with hydrophobic amino acid residues. It was shown that by these means the overall hydrophobic interaction in the protein core was increased and that an increase of thermostability of the target protein was achieved. Further developments in the field of stabilization of protein structures were reviewed by Lee, B., and Vasmatzis, G., Current Opinion Biotechn. 8 (1997) 423-428.

With the aim of applying this knowledge to the development of the desired T7 variants, high resolution x-ray structures of T7 RNA polymerase deposited in data banks were carefully inspected. Candidate sites in the protein structures were identified and sites were selected where certain mutations could improve the stability of the enzyme. The designed variants were synthesized, cloned, expressed and purified. The stability of the enzyme variants was examined and compared with the stability of the wild-type enzyme. Table 3 in Example 1 summarizes the mutations considered in the experimental work underlying the present invention.

To determine of the stability of wild-type T7 polymerase and T7 variants two parameters were examined: (i) the half-life time under a predetermined temperature regime, and (ii) the melting temperature ($T_m$).

In yet more detail, the present invention embodies the following items.

1. A variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference,
   wherein the variant comprises a polypeptide of the wild-type reference in which at least one amino acid and up to four amino acids at different positions is/are substituted,
   wherein a different amino acid substitutes for an amino acid selected from the group consisting of Val426, Ser633, Val650, Thr654, Ala702, and Val795, numbered from the N-terminus of the wild-type reference, and
   wherein the different amino acid is selected from the group consisting of
      Leu, Ile and Phe when the different amino acid substitutes for Val426 (Val426Leu, Val426Ile, Val426Phe),
      Val and Met when the different amino acid substitutes for Ser633 (Ser633Val, Ser633Met),
      Leu when the different amino acid substitutes for Val650 (Val650Leu),
      Leu when the different amino acid substitutes for Thr654 (Thr654Leu),
      Val when the different amino acid substitutes for Ala702 (Ala702Val),
      Ile when the different amino acid substitutes for Val795 (Val795Ile).
2. The T7 variant according to item 1, wherein a different amino acid substitutes for an amino acid selected from the group consisting of Val426, Val650, Ala702, and Val795.
3. The T7 variant according to item 2, wherein four amino acids at different positions are substituted, and the different amino acids are Val426Leu, Val650Leu, Ala702Val, and Val795Ile.
4. The T7 variant according to item 1, wherein a different amino acid substitutes for an amino acid selected from the group consisting of Val426, Ala702, and Val795, and wherein up to three amino acids at different positions is/are substituted.
5. The T7 variant according to item 4, wherein two or three amino acids at different positions are substituted, and the different amino acids are selected from the group consisting of Val426Leu, Ala702Val, and Val795Ile.
6. The T7 variant according to item 4, wherein three amino acids at different positions are substituted and the different amino acids are Val426Leu, Ala702Val, and Val795Ile.
7. The T7 variant according to any of the items 1 to 6, additionally comprising a tag (affinity tag) capable of specifically binding to an affinity chromatography matrix.
8. The T7 variant according to any of the items 1 to 7, wherein the affinity tag is a Histidine tag.
9. The T7 variant according to item 8, wherein the Histidine tag is a C-terminal tag.
10. The T7 variant according to item 8, wherein the Histidine tag is a N-terminal tag.
11. The T7 variant according to item 10, additionally comprising a linker sequence linking the Histidine tag with the amino acid corresponding to Met1 or Asn2 of SEQ ID NO: 2.
12. The T7 variant according to item 11, wherein the linker sequence consists of between 1 and 4 amino acids.
13. The T7 variant according to item 12, wherein the linker sequence consists of between 1 and 2 amino acids.
14. The T7 variant according to any of the items 1 to 13, wherein at 50° C. the half-life time of the variant is between 12 min and about 320 min, and particularly between 12 min and about 312 min; preferably, the T7 variant comprises (i) a single amino acid substitution selected from the group consisting of [Val426Leu], [Val426Ile], [Val426Phe], [Ser633Met], [Val650Leu], [Thr654Leu], [Ala702Val], and [Val795Ile], or (ii) a double amino acid substitution selected from the group consisting of [Ala702Val, Val795Ile], [Val426Leu, Ala702Val], and [Val426Leu, Val795Ile], or (iii) the triple amino acid substitution [Val426Leu, Ala702Val, Val795Ile], or (iv) the quadruple amino acid substitution [Val426Leu, Val650Leu, Ala702Val, Val795Ile].
15. The T7 variant according to item 14, wherein the half-life time is between about 20 min and about 320 min, and particularly between 20 min and about 312 min.
16. The T7 variant according to item 14, wherein the half-life time is between about 30 min and about 320 min, and particularly between about 30 min and about 312 min.
17. The T7 variant according to item 14, wherein the half-life time is between about 40 min and about 320 min, and particularly between about 40 min and about 312 min.
18. The T7 variant according to item 14, wherein the half-life time is between about 60 min and about 320 min, and particularly between about 60 min and about 312 min.
19. The T7 variant according to item 14, wherein the half-life time is about 320 min.
20. The T7 variant according to item 14, wherein the half-life time is about 312 min.
21. A method to produce a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said method comprising the steps of
   (a) selecting an amino acid from the group consisting of Val426, Ser633, Val650, Thr654, Ala702, and Val795, numbered from the N-terminus of the wild-type reference;
   (b) substituting a selected amino acid with a different amino acid to form a T7 variant, wherein the different amino acid is selected from the group consisting of
      Leu, Ile and Phe when the different amino acid substitutes for Val426 (Val426Leu, Val426Ile, Val426Phe),
      Val and Met when the different amino acid substitutes for Ser633 (Ser633Val, Ser633Met), Leu when the different amino acid substitutes for Val650 (Val650Leu),
Leu when the different amino acid substitutes for Thr654 (Thr654Leu),
Val when the different amino acid substitutes for Ala702 (Ala702Val),
Ile when the different amino acid substitutes for Val795 (Val795Ile),
wherein at least one amino acid of the wild-type reference and up to four amino acids at different positions is/are substituted;
(c) expressing a nucleic acid molecule with a nucleotide sequence encoding the T7 variant with the substituted amino acids of step (b) in an expression system transformed host organism, and isolating the expressed T7 variant from the expression system host organism;
thereby producing the T7 variant.

22. The method of item 21, wherein the expression system is selected from the group consisting of a transformed host organism and a cell-free expression system.

23. The method according to any of the items 21 and 22, wherein in step (c) the nucleic acid molecule encodes a T7 variant according to any of the items 1 to 20.

24. A method to produce a nucleic acid molecule with a nucleotide sequence encoding a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said method comprising the steps of
(a) reverse transcribing an amino acid sequence of a polypeptide according to any of the items 1 to 20 or an amino acid sequence of a polypeptide obtainable by the method according to any of the items 21 to 23, thereby obtaining a nucleic acid sequence; followed by
(b) synthesizing a nucleic acid molecule with the nucleic acid sequence obtained after performing step (a);
thereby producing the nucleic acid molecule encoding the T7 variant.

25. A nucleic acid molecule with a nucleotide sequence encoding a variant polypeptide of T7 RNA polymerase (T7 variant), said T7 variant being characterized by (i) a DNA-dependent RNA polymerase activity, (ii) an enhanced thermostability compared to the 883-amino acid T7 RNA polymerase polypeptide of SEQ ID NO: 2 (wild-type reference), and (iii) a different composition of amino acids compared to the wild-type reference, said nucleic acid being obtainable by the method of item 24.

26. The nucleic acid molecule according to item 25, wherein the nucleotide sequence of said nucleic acid comprises a sequence selected from the group consisting of SEQ ID NO: 9, SEQ ID NO: 11, SEQ ID NO: 19, SEQ ID NO: 21, SEQ ID NO: 23, SEQ ID NO: 25, SEQ ID NO: 29, SEQ ID NO: 37, SEQ ID NO: 39, SEQ ID NO: 41, SEQ ID NO: 43, and SEQ ID NO: 47.

27. An expression vector comprising a nucleic acid molecule according to any of the items 25 and 26, wherein said nucleic acid molecule is functionally linked to one or more nucleotide sequences capable of controlling transcription and/or translation.

28. A host organism capable of recombinant expression of a polypeptide, wherein said host organism is transformed with an expression vector according to item 27.

29. A method to synthesize a RNA molecule, comprising the steps of
(a) providing a template DNA molecule comprising a T7 promoter, said T7 promoter being functionally linked to a target nucleotide sequence to be transcribed;
(b) contacting the template DNA of step (a) with a variant polypeptide of T7 RNA polymerase (T7 variant) according to any of the items 1 to 20 or a T7 variant obtainable by the method according to any of the items 21 to 23; followed by
(c) incubating the template DNA and the T7 variant in the presence of ribonucleoside triphosphates;
thereby synthesizing the RNA molecule.

30. The method according to item 29, wherein step (c) is performed at a temperature from 4° C. to 55° C., more preferred at a temperature from 18° C. to 50° C., and even more preferred at a temperature from 37° C. to 50° C.

31. A composition comprising (i) a template DNA molecule, the template DNA molecule comprising a T7 promoter which is functionally coupled to a target nucleotide sequence to be transcribed, (ii) ribonucleoside triphosphates, (iii) an aqueous buffer, and (iv) a variant polypeptide of T7 RNA polymerase (T7 variant) according to any of the items 1 to 20 or a T7 variant obtainable by the method according to any of the items 21 to 23.

32. Use of a composition according to item 31 in a method according to any of the items 29 and 30.

33. A kit comprising, in separate containers, a variant polypeptide of T7 RNA polymerase (T7 variant) according to any of the items 1 to 20 or a T7 variant obtainable by the method according to any of the items 21 to 23, and an aqueous buffer with one or more ribonucleoside triphosphates.

34. Use of a kit according to item 33 in a method according to any of the items 29 and 30.

The following examples and sequence listing are provided to aid the understanding of the present invention, the true scope of which is set forth in the appended claims. It is understood that modifications can be made in the procedures set forth without departing from the spirit of the invention.

Description of the Sequence Listing

SEQ ID NO: 1 DNA (=nucleic acid; here and in the following SEQ ID NO items to be read as DNA, if not indicated otherwise) sequence encoding wild-type T7 DNA-dependent RNA polymerase, including start codon encoding N-terminal Methionine; corresponding to #1 in Table 3.

SEQ ID NO: 2 Wild-type T7 DNA-dependent RNA polymerase, amino acid sequence including N-terminal Methionine; corresponding to #1 in Table 3.

SEQ ID NO: 3 DNA sequence encoding the A319S variant of T7 DNA-dependent RNA polymerase, including start codon encoding N-terminal Methionine; corresponding to #2 in Table 3.

SEQ ID NO: 4 A319S variant of T7 DNA-dependent RNA polymerase, amino acid sequence including N-terminal Methionine; corresponding to #2 in Table 3.

SEQ ID NO: 5 DNA sequence encoding the A319V variant of T7 DNA-dependent RNA polymerase, including start codon encoding N-terminal Methionine; corresponding to #3 in Table 3.

SEQ ID NO: 6 A319V variant of T7 DNA-dependent RNA polymerase, amino acid sequence including N-terminal Methionine; corresponding to #3 in Table 3.

SEQ ID NO: 7 DNA sequence encoding the A319P variant of T7 DNA-dependent RNA polymerase, including start codon encoding N-terminal Methionine; corresponding to #4 in Table 3.

SEQ ID NO: 8 A319P variant of T7 DNA-dependent RNA polymerase, amino acid sequence including N-terminal Methionine; corresponding to #4 in Table 3.

SEQ ID NO: 9 DNA sequence encoding the V426L variant of T7 DNA-dependent RNA polymerase, including start codon encoding N-terminal Methionine; corresponding to #5 in Table 3.

SEQ ID NO: 10 V426L variant of T7 DNA-dependent RNA polymerase, amino acid sequence including N-terminal Methionine; corresponding to #5 in Table 3.

SEQ ID NO: 11 DNA sequence encoding the V426I variant of T7 DNA-dependent RNA polymerase, including start codon encoding N-terminal Methionine; corresponding to #6 in Table 3.

SEQ ID NO: 12 V426I variant of T7 DNA-dependent RNA polymerase, amino acid sequence including N-terminal Methionine; corresponding to #6 in Table 3.

SEQ ID NO: 13 DNA sequence encoding the V426F variant of T7 DNA-dependent RNA polymerase, including start codon encoding N-terminal Methionine; corresponding to #7 in Table 3.

SEQ ID NO: 14 V426F variant of T7 DNA-dependent RNA polymerase, amino acid sequence including N-terminal Methionine; corresponding to #7 in Table 3.

SEQ ID NO: 15 DNA sequence encoding the S633V variant of T7 DNA-dependent RNA polymerase, including start codon encoding N-terminal Methionine; corresponding to #10 in Table 3.

SEQ ID NO: 16 S633V variant of T7 DNA-dependent RNA polymerase, amino acid sequence including N-terminal Methionine; corresponding to #10 in Table 3.

SEQ ID NO: 17 DNA sequence encoding the S633L variant of T7 DNA-dependent RNA polymerase, including start codon encoding N-terminal Methionine; corresponding to #11 in Table 3.

SEQ ID NO: 18 S633L variant of T7 DNA-dependent RNA polymerase, amino acid sequence including N-terminal Methionine; corresponding to #11 in Table 3.

SEQ ID NO: 19 DNA sequence encoding the S633M variant of T7 DNA-dependent RNA polymerase, including start codon encoding N-terminal Methionine; corresponding to #12 in Table 3.

SEQ ID NO: 20 S633M variant of T7 DNA-dependent RNA polymerase, amino acid sequence including N-terminal Methionine; corresponding to #12 in Table 3.

SEQ ID NO: 21 DNA sequence encoding the V650L variant of T7 DNA-dependent RNA polymerase, including start codon encoding N-terminal Methionine; corresponding to #13 in Table 3.

SEQ ID NO: 22 V650L variant of T7 DNA-dependent RNA polymerase, amino acid sequence including N-terminal Methionine; corresponding to #13 in Table 3.

SEQ ID NO: 23 DNA sequence encoding the T654L variant of T7 DNA-dependent RNA polymerase, including start codon encoding N-terminal Methionine; corresponding to #14 in Table 3.

SEQ ID NO: 24 T654L variant of T7 DNA-dependent RNA polymerase, amino acid sequence including N-terminal Methionine; corresponding to #14 in Table 3.

SEQ ID NO: 25 DNA sequence encoding the A702V variant of T7 DNA-dependent RNA polymerase, including start codon encoding N-terminal Methionine; corresponding to #15 in Table 3.

SEQ ID NO: 26 A702V variant of T7 DNA-dependent RNA polymerase, amino acid sequence including N-terminal Methionine; corresponding to #15 in Table 3.

SEQ ID NO: 27 DNA sequence encoding the L705I variant of T7 DNA-dependent RNA polymerase, including start codon encoding N-terminal Methionine; corresponding to #16 in Table 3.

SEQ ID NO: 28 L705I variant of T7 DNA-dependent RNA polymerase, amino acid sequence including N-terminal Methionine; corresponding to #16 in Table 3.

SEQ ID NO: 29 DNA sequence encoding the V795I variant of T7 DNA-dependent RNA polymerase, including start codon encoding N-terminal Methionine; corresponding to #18 in Table 3.

SEQ ID NO: 30 V795I variant of T7 DNA-dependent RNA polymerase, amino acid sequence including N-terminal Methionine; corresponding to #18 in Table 3.

SEQ ID NO: 31 DNA sequence encoding the L809F variant of T7 DNA-dependent RNA polymerase, including start codon encoding N-terminal Methionine; corresponding to #19 in Table 3.

SEQ ID NO: 32 L809F variant of T7 DNA-dependent RNA polymerase, amino acid sequence including N-terminal Methionine; corresponding to #19 in Table 3.

SEQ ID NO: 33 DNA sequence encoding the F814W variant of T7 DNA-dependent RNA polymerase, including start codon encoding N-terminal Methionine; corresponding to #20 in Table 3.

SEQ ID NO: 34 F814W variant of T7 DNA-dependent RNA polymerase, amino acid sequence including N-terminal Methionine; corresponding to #20 in Table 3.

SEQ ID NO: 35 DNA sequence encoding the M861W variant of T7 DNA-dependent RNA polymerase, including start codon encoding N-terminal Methionine; corresponding to #21 in Table 3.

SEQ ID NO: 36 M861W variant of T7 DNA-dependent RNA polymerase, amino acid sequence including N-terminal Methionine; corresponding to #21 in Table 3.

SEQ ID NO: 37 DNA sequence encoding the A702V, V795I variant (double mutant) of T7 DNA-dependent RNA polymerase, including start codon encoding N-terminal Methionine; corresponding to #22 in Table 3.

SEQ ID NO: 38 A702V, V795I variant (double mutant) of T7 DNA-dependent RNA polymerase, amino acid sequence including N-terminal Methionine; corresponding to #22 in Table 3.

SEQ ID NO: 39 DNA sequence encoding the V426L, A702V variant (double mutant) of T7 DNA-dependent RNA polymerase, including start codon encoding N-terminal Methionine; corresponding to #23 in Table 3.

SEQ ID NO: 40 V426L, A702V variant (double mutant) of T7 DNA-dependent RNA polymerase, amino acid sequence including N-terminal Methionine; corresponding to #23 in Table 3.

SEQ ID NO: 41 DNA sequence encoding the V426L, V795I variant (double mutant) of T7 DNA-dependent RNA polymerase, including start codon encoding N-terminal Methionine; corresponding to #24 in Table 3.

SEQ ID NO: 42 V426L, V795I variant (double mutant) of T7 DNA-dependent RNA polymerase, amino acid sequence including N-terminal Methionine; corresponding to #24 in Table 3.

SEQ ID NO: 43 DNA sequence encoding the V426L, A702V, V795I variant (triple mutant) of T7 DNA-dependent RNA polymerase, including start codon encoding N-terminal Methionine; corresponding to #25 in Table 3.

SEQ ID NO: 44 V426L, A702V, V795I variant (triple mutant) of T7 DNA-dependent RNA polymerase, amino acid sequence including N-terminal Methionine; corresponding to #25 in Table 3.

SEQ ID NO: 45 DNA sequence encoding the V426L, S633M, A702V, V795I variant (quadruple mutant) of T7 DNA-dependent RNA polymerase, including start codon encoding N-terminal Methionine; corresponding to #26 in Table 3.

SEQ ID NO: 46 V426L, S633M, A702V, V795I variant (quadruple mutant) of T7 DNA-dependent RNA polymerase, amino acid sequence including N-terminal Methionine; corresponding to #26 in Table 3.

SEQ ID NO: 47 DNA sequence encoding the V426L, V650L, A702V, V795I variant (quadruple mutant) of T7 DNA-dependent RNA polymerase, including start codon encoding N-terminal Methionine; corresponding to #27 in Table 3.

SEQ ID NO: 48 V426L, V650L, A702V, V795I variant (quadruple mutant) of T7 DNA-dependent RNA polymerase, amino acid sequence including N-terminal Methionine; corresponding to #27 in Table 3.

SEQ ID NO: 49 DNA sequence encoding the V426L, S633M, V650L, A702V, V795I variant (quintuple mutant) of T7 DNA-dependent RNA polymerase, including start codon encoding N-terminal Methionine; corresponding to #28 in Table 3.

SEQ ID NO: 50 V426L, S633M, V650L, A702V, V795I variant (quintuple mutant) of T7 DNA-dependent RNA polymerase, amino acid sequence including N-terminal Methionine; corresponding to #28 in Table 3.

SEQ ID NO: 51 DNA sequence encoding N-terminal Histidine tag (His6) (SEQ ID NO: 54) with linker sequence, fused to the first two N-terminal amino acids of T7 (Met and Asn).

SEQ ID NO: 52 Amino acid sequence of N-terminal Histidine (His6) tag (SEQ ID NO: 54) with linker sequence, fused to the first two N-terminal amino acids of T7 (Met and Asn).

Example 1

Design of Amino Acid Exchange Mutations in the T7 Polypeptide

X-ray structures of T7 RNA polymerase deposited in the Protein Data Bank (codes: 1cez [referring to Cheetham, G. M. T., et al., Nature 399 (1999) 80-83], and 1s77 [referring to Yin, Y. W., and Steitz, T. A., Cell 116 (2004) 393-404]) were inspected to identify candidate sites for the introduction of mutations to increase the stability of the protein.

Selected positions of the T7 wild-type amino acid sequence (according to SEQ ID NO: 2) are shown in Table 1 which also provides amino acid substitution mutations expected to increase the stability of the T7 polymerase protein. The underlying rationale of the design of the mutations is also indicated.

Most of the substituting amino acids were selected either to fill hydrophobic cavities in the core or to stabilize loops located at the surface of the enzyme.

TABLE 1

Amino acid mutations of T7 RNA polymerase: Design of an enzyme with increased thermostability

| Amino acid, WT | Position | Mutation | Rationale |
|---|---|---|---|
| Ala | 319 | Ser, Val, Pro | Fill cavity in protein core |
| Val | 426 | Leu, Ile, Phe, Trp | Fill cavity in protein core |
| Val | 629 | Pro | Stabilize loop |
| Ser | 633 | Val, Leu, Met | Stabilize loop |
| Val | 650 | Leu | Stabilize loop |

TABLE 1-continued

Amino acid mutations of T7 RNA polymerase: Design of an enzyme with increased thermostability

| Amino acid, WT | Position | Mutation | Rationale |
|---|---|---|---|
| Thr | 654 | Leu | Stabilize loop |
| Ala | 702 | Val | Fill cavity in protein core |
| Leu | 705 | Ile | Fill cavity in protein core |
| Leu | 791 | Phe | Fill cavity in protein core |
| Val | 795 | Ile | Fill cavity in protein core |
| Leu | 809 | Phe | Fill cavity in protein core |
| Phe | 814 | Trp | Fill cavity in protein core |
| Met | 861 | Trp | Fill cavity in protein core |

In order to provide a coding sequence for any of the T7 mutants shown, the nucleotide sequence of SEQ ID NO: 1 encoding the T7 wild type reference polypeptide was used as a basis. The nucleotide codons corresponding to the amino acid residues at the positions indicated in Table 1 were mutated, in order to encode the changed amino acid at the respective position. Mutations were preferably designed in accordance with the codon usage bias of *E. coli* class II genes (Hénaut, A., and Danchin, A., Analysis and Predictions from *Escherichia coli* sequences. *Escherichia coli* and *Salmonella*, Vol. 2, Ch. 114 (1996) 2047-2066, Neidhardt F C ed., ASM press, Washington, D.C.), as given in Table 2.

TABLE 2

Codon usage in *E. coli*

| | | Class | | |
|---|---|---|---|---|
| Amino acid | Codon | I | II | III |
| Phe | TTT | 55.09 | 29.08 | 67.14 |
|  | TTC | 44.91 | 70.92 | 32.86 |
| Leu | TTA | 10.99 | 3.44 | 20.09 |
|  | TTG | 13.02 | 5.47 | 15.05 |
| Ser | TCT | 13.26 | 32.41 | 19.63 |
|  | TCC | 15.02 | 26.56 | 11.34 |
|  | TCA | 10.83 | 4.79 | 22.09 |
|  | TCG | 16.88 | 7.39 | 10.6 |
| Tyr | TAT | 54.42 | 35.23 | 69.6 |
|  | TAC | 45.58 | 64.77 | 30.4 |
| Stop | TAA | | | |
|  | TAG | | | |
| Cys | TGT | 40.9 | 38.85 | 55.71 |
|  | TGC | 59.1 | 61.15 | 44.29 |
| Stop | TGA | | | |
| Trp | TGG | 100 | 100 | 100 |
| Ile | ATT | 51.2 | 33.49 | 47.57 |
|  | ATC | 44.37 | 65.94 | 26.65 |
|  | ATA | 4.43 | 0.57 | 25.78 |
| Met | ATG | 100 | 100 | 100 |
| Thr | ACT | 14.85 | 29.08 | 26.83 |
|  | ACC | 46.83 | 53.6 | 24.45 |
|  | ACA | 10.52 | 4.67 | 27.93 |
|  | ACG | 27.81 | 12.65 | 20.8 |
| Asn | AAT | 40.87 | 17.25 | 64.06 |
|  | AAC | 59.13 | 82.75 | 35.94 |
| Lys | AAA | 75.44 | 78.55 | 72.21 |
|  | AAG | 24.56 | 21.45 | 27.79 |
| Ser | AGT | 13.96 | 4.52 | 18.73 |
|  | AGC | 30.04 | 24.33 | 17.61 |
| Arg | AGA | 1.75 | 0.62 | 15.63 |
|  | AGG | 1.54 | 0.29 | 9.96 |
| Leu | CTT | 9.7 | 5.56 | 19 |
|  | CTC | 10.4 | 8.03 | 9.04 |
|  | CTA | 3.09 | 0.83 | 6.81 |
|  | CTG | 52.79 | 76.67 | 29.99 |
| Pro | CCT | 13.71 | 11.23 | 28.3 |
|  | CCC | 11.19 | 1.63 | 16.26 |
|  | CCA | 18.63 | 15.25 | 31.5 |
|  | CCG | 56.47 | 71.89 | 23.94 |

TABLE 2-continued

Codon usage in E. coli

| Amino acid | Codon | Class I | Class II | Class III |
|---|---|---|---|---|
| His | CAT | 56.8 | 29.77 | 61.69 |
| | CAC | 43.2 | 70.23 | 38.31 |
| Gln | CAA | 33.4 | 18.65 | 37.06 |
| | CAG | 66.6 | 81.35 | 62.94 |
| Arg | CGT | 38.99 | 64.25 | 26.05 |
| | CGC | 42.23 | 32.97 | 21.94 |
| | CGA | 5.52 | 1.07 | 12.8 |
| | CGG | 8.97 | 0.8 | 13.62 |
| Val | GTT | 23.74 | 39.77 | 34.33 |
| | GTC | 22.48 | 13.45 | 18.95 |
| | GTA | 14.86 | 19.97 | 21.78 |
| | GTG | 38.92 | 26.81 | 24.94 |
| Ala | GCT | 14.52 | 27.54 | 22.86 |
| | GCC | 27.62 | 16.14 | 23.67 |
| | GCA | 19.63 | 24.01 | 31.27 |
| | GCG | 38.23 | 32.3 | 22.19 |
| Asp | GAT | 62.83 | 46.05 | 70.47 |
| | GAC | 37.17 | 53.95 | 29.53 |
| Glu | GAA | 68.33 | 75.35 | 66.25 |
| | GAG | 31.67 | 24.65 | 33.75 |
| Gly | GGT | 32.91 | 50.84 | 31.79 |
| | GGC | 43.17 | 42.83 | 24.51 |
| | GGA | 9.19 | 1.97 | 24.75 |
| | GGG | 14.74 | 4.36 | 18.95 |

The genes which served as the basis for the data in Table 2 were clustered by using factorial correspondence analysis into three classes. Class I contains genes involved in most metabolic processes. Class II genes correspond to genes highly and continuously expressed during exponential growth. Class III genes are implicated in horizontal transfer of DNA. One can see that the distribution of codons in class III genes is more or less even, whereas it is extremely biased in class II genes (in particular, codons terminated in A are selected against).

The mutations on the codon level which were introduced in the T7 coding sequence are shown in Table 3.

TABLE 3

T7 polymerase and variants thereof

| # | T7 enzyme/variant | WT codon | Mutated codon | SEQ ID NO: |
|---|---|---|---|---|
| 1 | Wild-type | — | | 1, 2 |
| 2 | Ala319Ser | GCG | AGC | 3, 4 |
| 3 | Ala319Val | GCG | GTT | 5, 6 |
| 4 | Ala319Pro | GCG | CCG | 7, 8 |
| 5 | Val426Leu | GTT | CTG | 9, 10 |
| 6 | Val426Ile | GTT | ATC | 11, 12 |
| 7 | Val426Phe | GTT | TTC | 13, 14 |
| 8 | Val426Trp | GTT | TGG | |
| 9 | Val629Pro | GTG | CCG | |
| 10 | Ser633Val | TCA | GTT | 15, 16 |
| 11 | Ser633Leu | TCA | CTG | 17, 18 |
| 12 | Ser633Met | TCA | ATG | 19, 20 |

TABLE 3-continued

T7 polymerase and variants thereof

| # | T7 enzyme/variant | WT codon | Mutated codon | SEQ ID NO: |
|---|---|---|---|---|
| 13 | Val650Leu | GTG | CTG | 21, 22 |
| 14 | Thr654Leu | ACC | CTG | 23, 24 |
| 15 | Ala702Val | GCT | GTT | 25, 26 |
| 16 | Leu705Ile | CTG | ATC | 27, 28 |
| 17 | Leu791Phe | CTT | TTC | |
| 18 | Val795Ile | GTA | ATC | 29, 30 |
| 19 | Leu809Phe | CTG | TTC | 31, 32 |
| 20 | Phe814Trp | TTC | TGG | 33, 34 |
| 21 | Met861Trp | ATG | TGG | 35, 36 |
| 22 | Ala702Val<br>Val795Ile | GCT<br>GTA | GTT<br>ATC | 37, 38 |
| 23 | Val426Leu<br>Ala702Val | GTT<br>GCT | CTG<br>GTT | 39, 40 |
| 24 | Val426Leu<br>Val795Ile | GTT<br>GTA | CTG<br>ATC | 41, 42 |
| 25 | Val426Leu<br>Ala702Val<br>Val795Ile | GTT<br>GCT<br>GTA | CTG<br>GTT<br>ATC | 43, 44 |
| 26 | Val426Leu<br>Ser633Met<br>Ala702Val<br>Val795Ile | GTT<br>TCA<br>GCT<br>GTA | CTG<br>ATG<br>GTT<br>ATC | 45, 46 |
| 27 | Val426Leu<br>Val650Leu<br>Ala702Val<br>Val795Ile | GTT<br>GTG<br>GCT<br>GTA | CTG<br>CTG<br>GTT<br>ATC | 47, 48 |
| 28 | Val426Leu<br>Ser633Met<br>Val650Leu<br>Ala702Val<br>Val795Ile | GTT<br>TCA<br>GTG<br>GCT<br>GTA | CTG<br>ATG<br>CTG<br>GTT<br>ATC | 49, 50 |

On the amino acid level, the T7 variants are shown in SEQ ID NOs: 4, 6, 8, 10, 12, 14, 16, 18, 20, 22, 24, 26, 28, 30, 32, 34, 36, 38, 40, 42, 44, 46, 48, and 50.

The nucleotide sequences encoding the mutated T7 polypeptides which were expressed in E. coli are shown in SEQ ID NOs: 3, 5, 7, 9, 11, 13, 15, 17, 19, 21, 23, 25, 27, 29, 31, 33, 35, 37, 39, 41, 43, 45, 47, and 49. The sequences are represented including the start codons for N-terminal Methionine but without any other additional artificial N-terminal structures such as His-tags.

Well-known to the art, a His-tag (in the literature also referred to as a polyHis-tag) is an amino acid motif in proteins that typically consists of at least six consecutive His residues (His6) (SEQ ID NO: 54). While the N-terminus of a T7 variant is preferred for the addition of the His-tag, the C-terminus of the polypeptide can serve as an alternative.

For clarification, a N-terminal His-tag can be located between the Methionine at the N-terminus of the respective variant T7 polypeptide and the subsequent amino acid according to the amino acid sequence of SEQ ID NO: 2, i.e., Asn. Alternatively, the His-tag can be appended to the N-terminal Methionine of the T7 variant. When appended at the C-terminus of the variant T7 polypeptide the His-tag forms the C-terminal amino acids.

The T7 variants were modified further such that each polypeptide contained a His-tag at its N-terminus to facilitate purification.

Apart from the Histidines the His-tag can additionally comprise further amino acids depending on the design of the nucleotide sequence encoding the His-tag. Thus, an oligonucleotide linker with restriction sites typically adds 1 to 5 further amino acids to the nucleotide fragment encoding the consecutive His residues in the His-tag.

The amino acid sequences of the T7 variants of Table 1 and the nucleic acid sequences encoding the T7 variants are shown in the sequence listing of this disclosure. No His-tags are shown as these may differ sequence-wise, depending on the particular cloning vector used. However, the differences concerning the number of Histidines and the linker sequence, according to the preferred embodiments, are not expected to have a technical impact on the T7 variants according to the invention.

Example 2

Cloning of Nucleic Acids Encoding Variants of T7 RNA Polymerase

All molecular biological procedures were performed according to standard methods (Sambrook J., Fritsch E. F., Maniatis T., (1989) *Molecular cloning: A Laboratory Manual second Edition*, B.27 Cold Spring Harbor Laboratory Press NY (USA)). Nucleotide sequences encoding the wild-type and the mutant T7 polypeptides were synthesized by a combinatorial synthesis strategy as described (van den Brulle, J., et al., Biotechniques 45(3) (2008) 340-343).

For expression of each of the T7 variants, the respective coding DNA sequence was cloned in appropriate expression vectors in such a way that the mutated T7 coding sequence is inserted in the right orientation under the control of an appropriate promoter, preferably an inducible promoter, particularly preferably the lac-, lacUV5-, tac- or T5 promoter. Preferred expression vectors are pUC plasmids with lac- or lacUV5 promoters or pKK plasmids. For clarification an exemplary coding sequence comprises a DNA encoding a polypeptide selected from any of SEQ ID NOs: 3, 5, 7, 9, 11, 13, 15, 17, 19, 21, 23, 25, 27, 29, 31, 33, 35, 37, 39, 41, 43, 45, 47, and 49 which optionally include a further modification such as a His-tag.

The synthesized genes were cloned in plasmid pUC18. The recipient strain for transformations was *E. coli* XL-1 blue. Transformed clones were grown at 37° C. in LB media containing ampicillin (100 µg/ml). Plasmids were isolated and digested using EcoRI and HindIII. The resulting fragments were subjected to agarose gel electrophoresis and the respective band corresponding to the variant T7 polymerase coding sequence was extracted. The isolated fragments were ligated into the expression plasmid pKKT5 (derived from pKK177-3 [Kopetzki, E., et al., Mol. Gen. Genet. 216 (1989) 149-155] by exchanging the tac-promoters with the T5-promoter derived from the plasmid pDS [Bujard, H., et al., Methods Enzymol. 155 (1987) 416-433]) which was digested with EcoRI and HindIII.

Plasmids were transformed into *E. coli* UT5600 (harboring plasmid pUBS520). Clones were grown at 37° C. in LB media containing ampicillin (100 µg/ml) and kanamycin (50 µg/ml).

Example 3

Expression and Purification of Variant T7 Polymerase Polypeptides

Transformed *E. coli* expression strains obtained as described in Example 2 were cultivated at 37° C. in LB media containing ampicillin (100 µg/ml) and kanamycin (50 µg/ml). Induction of recombinant expression was performed at an optical density of 0.7 (measured at 578 nm) by adding IPTG in a final concentration of 1 mM. After 5 hours the cells were harvested by centrifugation and frozen at −20° C.

His-tagged wild-type T7 polymerase and T7 variants were purified separately to homogeneity using metal chelate affinity matrix chromatography. Typically, wet frozen cells (2.1 g) were suspended in 30 ml buffer A (50 mM Tris/HCl, pH 8.1 [pH adjusted at room temperature], 1 M NaCl). To the suspension 315 µl of a lysozyme solution (10 mg/ml) were added. After incubation at room temperature for 15 min, the cells were sonicated (6×2 min). The cell debris was removed by centrifugation at 5,000 rpm for 15 min. A fraction of the supernatant (25 ml) was applied onto a Ni-chelating Sepharose column (1 ml). The column was washed using buffer A which additionally contained 10 mM imidazole. His-tagged polypeptides were eluted in a linear gradient (10 mM-500 mM imidazole in buffer A). Enzyme-containing fractions were pooled. After dialysis against storage buffer (10 mM potassium phosphate, 200 mM KCl, 0.1 mM EDTA, 30 mM mercaptoethanol, 50% glycerol, 0.1% Tween 20, pH 7.9) the pools were stored at −20° C.

Example 4

Analysis of DNA-Dependent RNA Polymerase Activity

A transcription-based non-radioactive assay was used to measure the activity of purified wild-type and variants of T7 RNA polymerase obtained as described in Example 3. The enzyme activity was measured in 40 µl reaction buffer (40 mM Tris/HCl, 6 mM $MgCl_2$, 1 mM NTP (each), 10 mM DTE, 2 mM spermidine, pH 8.0, 1 µg pSPT18 cleaved with SspI). T7 wild-type or T7 variant polymerase enzyme was added in diluted form. After incubation at 37° C. for 30 min. EDTA (0.4 M, 4 µl) was added to stop the reaction. RNA quantification was done using Quant-iT RNA Assay (Invitrogen) on a LC480 Light Cycler platform (Roche Applied Science, Roche Diagnostics GmbH, Mannheim). As a reference enzyme commercially available T7 RNA polymerase was used (Roche Applied Science, Roche Diagnostics GmbH, Mannheim).

Example 5

Analysis of Thermostability: Half-Life Time

To determine the stability of wild-type T7 polymerase and T7 variants the half-life time was determined as a first parameter. Samples of wild-type enzyme and purified variants (see Example 3) were incubated in storage buffer (10 mM potassium phosphate, 200 mM KCl, 0.1 mM EDTA, 30 mM mercaptoethanol, 50% glycerol, 0.1% Tween 20, pH 7.9) at 50° C. At different time points (10, 20 and 30 min) samples were taken and the residual enzyme activity was measured as described in Example 3. The half-life time $T_{1/2}$ expressed as a number of minutes [min] means that at this time point the activity of the respective T7 variant is 50% of the activity at the time point when the experiment was started, i.e., the exposure to 50° C. was applied. Table 4 summarizes results of the measurements.

TABLE 4

Half-life times at 50° C. of wild-type T7 RNA polymerase and T7 variants (single mutations and combination mutations)

| # | T7 enzyme | $T_{1/2}$ [min] |
|---|---|---|
| | Reference | |
| 1 | Wild-type | 6.0-9.7 |
| | Single amino acid substitution | |
| 2 | Ala319Ser | no activity |
| 3 | Ala319Val | 8.5 |
| 4 | Ala319Pro | no activity |
| 5 | Val426Leu | 25.0 |
| 6 | Val426Ile | 17.0 |
| 7 | Val426Phe | 12.0 |
| 8 | Val426Trp | 0.4 |
| 9 | Val629Pro | no activity |
| 10 | Ser633Val | 7.3 |
| 11 | Ser633Leu | 5.3 |
| 12 | Ser633Met | 13.0 |
| 13 | Val650Leu | 13.0 |
| 14 | Thr654Leu | 13.0 |
| 15 | Ala702Val | 22.0 |
| 16 | Leu705Ile | 10.0 |
| 17 | Leu791Phe | no activity |
| 18 | Val795Ile | 29.0 |
| 19 | Leu809Phe | 7.7 |
| 20 | Phe814Trp | 1.9 |
| 21 | Met861Trp | 5.5 |
| | Double amino acid substitution | |
| 22 | Ala702Val Val795Ile | 22.0 |
| 23 | Val426Leu Ala702Val | 39.0 |
| 24 | Val426Leu Val795Ile | 40.0 |
| | Triple amino acid substitution | |
| 25 | Val426Leu Ala702Val Val795Ile | 312.0 |
| | Quadruple amino acid substitution | |
| 26 | Val426Leu Ser633Met Ala702Val Val795Ile | no activity |
| 27 | Val426Leu Val650Leu Ala702Val Val795Ile | 64.0 |
| | Quintuple amino acid substitution | |
| 28 | Val426Leu Ser633Met Val650Leu Ala702Val Val795Ile | no activity |

Designations of mutants are the same as in Table 3.

With regards to half-life times at 50° C., the inventors observed several surprising effects. Firstly, there were single amino acid exchanges without noticeable impact on thermostability, i.e., mutations which did not cause a substantial difference compared to the wild-type reference (#1). In this first group all T7 variants with a T½ value between 5 and 12 (including 5 and 12) were combined. The first group comprises the mutations according to ##3, 7, 10, 11, 16, 19, and 21 as shown in Table 4.

A second group of T7 variants was found in which the mutants had even shorter half-life times at 50° C., compared to the wild-type reference. Additionally, mutants which had lost enzymatic activity completely were combined in the second group. The second group comprises the mutations according to ##2, 4, 8, 9, 17, 20, 26, and 28 as shown in Table 4.

A third group of amino acid exchange mutations was found to enhance half-life time at 50° C. over the values found for the wild-type reference. A value greater than 12 was considered as indicating a substantial increase of thermostability in the respective T7 variant. The third group comprises the mutations according to ##5, 6, 12, 13, 14, 15, 18, 22, 23, 24, 25 and 27 as shown in Table 4.

Surprisingly, some amino acid substitutions which, according to theoretical predictions, were predicted to have a desired positive effect on thermostability did not lead to the expected results.

It was noted that mutations at the position Ala319 (see Table 1) belonged to either the first or the second group. According to the theory, these mutations were expected to fill a hydrophobic cavity and thereby increase internal Van-der-Waals forces within the core of the variant T7 polypeptide. Remarkably, the mutation of Ala319 to Val (#3 in Table 4) leaves the RNA polymerase activity intact but without having any noticeable impact on the variant's half-life time at 50° C. But at this position changes to Ser or Pro (#2, #4 in Table 4) abolish enzymatic activity. This finding was interpreted as an indication of more complex intramolecular interactions which impact on the structure and/or enzymatic function of T7 polymerase.

Further results were found at position Val426 which was another candidate residue to be exchanged for generating increased van-der-Waals forces in a cavity of the protein core. In line with the prediction, changing Val426 to Leu, Ile or Phe (#5, #6, #7 in Table 4) produced a variant with enhanced thermostability. But the mutation Val426Trp (#8 in Table 4) unexpectedly destabilized the polymerase enzyme. The same was observed for Leu791Phe (#17 in Table 4) and, although to a somewhat lesser extent, for Phe814Trp (#20 in Table 4).

The results obtained for the further mutations Leu705Ile (#16 in Table 4), Leu809Phe (#19 in Table 4) and Met861Trp (#21 in Table 4) did not provide an indication for enhanced thermostability.

Thus, with regards to the approach of increasing van-der-Waals forces in internal hydrophobic cavities, the general theoretical prediction of thermostabilization could not be verified at this point. Rather, the results shown in Table 4 demonstrate that (i) only a subgroup of the sites predicted to be suitable for the desired class of mutations is amenable to amino acid substitutions which actually lead to enhanced thermostability, (ii) there is no means at hand to pre-select this subgroup, and (iii) no prediction can be made which particular amino acid will be effective and produce the desired technical effect.

The same appears to apply to mutations designed to stabilize loop structures. Among six different mutations tested, one (Val629Pro) (#9 in Table 4) completely abolishes enzymatic activity, two (Ser633Val, Ser633Leu; #10 and #11 in Table 4) do not show profound effects, and three (Ser633Met, Val650Leu, and Thr654Leu; #12, #13 and #14 in Table 4) increase thermostability, however not as markedly as mutations of the third group directed to hydrophobic cavities. Again, one position (Ser633; #10, #11, and #12) stands out in that mutations unexpectedly lead to different effects.

Three mutations targeting stabilization of hydrophobic cavities produced results which stood out: Val426Leu, Ala702Val, and Val795Ile (#5, 15, and 18 in Table 4). The three mutations were combined in double and triple mutant variants. Interestingly, all combinations result in functional polymerase enzymes with increased thermostability when compared with the wild-type reference. Two double mutant combinations (#23 and #24 in Table 4) showed an even further increased thermostability which could be attributed to an additive effect. One double mutant combination (#22 in Table 4) suggests a polar mechanism in that the quantitative effect Ala702Val mutation seems to override the effect of the Val795Ile mutation. However, most strikingly, upon combination of the mutations in a triple mutant a synergistic effect was observed in that thermostability was increased by about one full order of magnitude (#25 in Table 4).

The synergistic effect is further illustrated by the fact that a variant with a quadruple mutant polypeptide which further includes the Val650Leu exchange (#27 in Table 4) shows a further additive effect. Regarding thermostability the effects seen with the quadruple mutant exceeded each of the double mutants but they fail to reach the high value observed with the triple mutant.

A further quadruple and a quintuple mutant variant (#26 and #28 in Table 4) illustrate that it is not possible to deliberately combine further mutations, i.e., that there are effects which render some or all of the combined mutations incompatible.

Example 6

Protein Thermal Unfolding Assay

The stability of wild-type T7 polymerase enzyme and variants of T7 RNA polymerase was further studied by way of determining protein thermal unfolding. The assay was performed essentially as by Yeh, A. P., et al., Acta Cryst. D62 (2006) 451-457, for measuring the unfolding transition of membrane proteins by fluorescent-probe binding in combination with real-time PCR instrumentation and using SYPRO Orange as reporter dye.

Accordingly, all assays were performed using a LC480 LIGHT CYCLER (Roche Applied Science). SYPRO Orange was obtained from Molecular Probes Inc. (Eugene, Oreg., USA) and was diluted 1:10 in DMSO. Protein samples (typically 2 μg) were in Bis-Tris-propane buffer (50-100 mM), pH 8.0 and contained diluted SYPRO Orange (1:1430). Excitation wave length was 483 nm, emission was measured at 568 nm.

Assays were performed in a temperature range starting from 37° C. up to 94° C. with a temperature ramp of 3.6° C./min. Protein thermal unfolding was measured in the absence (Buffer A) or presence (Buffer B) of 50% [v/v] glycerol (see Table 5).

TABLE 5

Protein thermal unfolding, $T_m$ determination

| # | T7 enzyme | $T_m$ [° C.] in Buffer A | $T_m$ [° C.] in Buffer B |
|---|---|---|---|
| Reference | | | |
| 1 | Wild-type | 50.0 | 51.5 |
| Single amino acid exchange | | | |
| 5 | Val426Leu | 52.5 | 52.5 |
| 13 | Val650Leu | 51.0 | n.d. |
| 15 | Ala702Val | 51.0 | n.d. |
| 18 | Val795Ile | 51.5 | n.d. |
| Triple amino acid exchange | | | |
| 25 | Val426Leu | n.d. (not determined) | 55.0 |
|  | Ala702Val | n.d. | n.d. |
|  | Val795Ile | n.d. | n.d. |

Designations of T7 variants are the same as in Table 4.

The data again show that the triple mutant T7 variant #25 exhibits the highest increase of the $T_m$, compared to the wild-type reference.

Example 7

Determination of Protein Concentration in Solutions

Protein concentrations were determined by measuring the optical density at 280 nm using a molar extinction coefficient of E280 nm=$1.4 \times 10^5$ $M^{-1}$ $cm^{-1}$ as described (He, B., et al., Protein Expr Purif 9 (1997) 142-151).

What is claimed is:

1. A variant T7 RNA polymerase, the variant T7 RNA polymerase having:
   (i) a DNA-dependent RNA polymerase activity,
   (ii) an enhanced thermostability compared to SEQ ID NO: 2 (wild-type reference), and
   (iii) a different composition of amino acids compared to the wild-type reference, wherein the variant T7 RNA polymerase comprises the polypeptide of the wild-type reference in which at least one amino acid and up to four amino acids are substituted, including the Val of Val426 numbered from the N-terminus of the wild-type reference wherein the substituted amino acid is selected from the group consisting of: Leu, Ile and Phe.

2. The variant T7 RNA polymerase according to claim 1, wherein the different amino acid substituted for the Val of Val426 is Leu.

3. The variant T7 RNA polymerase according to claim 1, wherein the different amino acid substituted for the Val of Val426 is Ile.

4. The variant T7 RNA polymerase according to claim 1, wherein the different amino acid substituted for the Val of Val426 is Phe.

5. A method for synthesizing an RNA molecule comprising the steps of
   (a) providing a template DNA molecule comprising a T7 promoter, the T7 promoter being functionally linked to a target nucleotide sequence to be transcribed;
   (b) contacting the template DNA of step (a) with the variant T7 RNA polymerase according to claim 1; followed by
   (c) incubating the template DNA and the T7 variant in the presence of ribonucleoside triphosphates, thereby synthesizing the RNA molecule.

6. A composition comprising:
   a template DNA molecule with a T7 promoter functionally coupled to a target nucleotide sequence to be transcribed, ribonucleoside triphosphates; and
   the variant polypeptide of T7 RNA polymerase according to claim 1.

7. A kit comprising, in separate containers:
   the variant polypeptide of T7 RNA polymerase according to claim 1; and
   a buffer wherein the buffer includes one or more ribonucleoside triphosphates.

8. The variant T7 RNA polymerase according to claim 1, wherein the variant includes the following four amino acid substitutions:
   the Val of Val426 substituted with Leu;
   the Val of Val650 substituted with Leu;
   the Ala of Ala702 substituted with Val; and
   the Val of Val795 substituted with Ile.

9. The variant T7 RNA polymerase according to claim 1, wherein the variant includes up to three amino acid substitutions selected from the group consisting of:
   the Val of Val426 substituted with an amino acid selected from the group consisting of: Leu, Ile and Phe;
   the Ala of Ala702 substituted with Val; and
   the Val of Val795 substituted with Ile.

10. The variant T7 RNA polymerase according to claim 1, wherein the variant includes two amino acid substitutions selected from the group consisting of:
    the Val of Val426 substituted with Leu;
    the Ala of Ala702 substituted with Val; and
    the Val of Val795 substituted with Ile.

11. The variant T7 RNA polymerase according to claim 1, wherein the variant includes the following three amino acid substitutions:
    the Val of Val426 substituted with Leu;
    the Ala of Ala702 substituted with Val; and
    the Val of Val795 substituted with Ile.

* * * * *